United States Patent
Grinberg et al.

(10) Patent No.: US 7,833,971 B2
(45) Date of Patent: Nov. 16, 2010

(54) USES OF CERBERUS, COCO AND DERIVATIVES THEREOF

(75) Inventors: Asya Grinberg, Boston, MA (US); John Knopf, Carlisle, MA (US); Ravindra Kumar, Shrewsbury, MA (US); Jasbir Seehra, Lexington, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 0 days.

(21) Appl. No.: 12/001,494

(22) Filed: Dec. 10, 2007

(65) Prior Publication Data

US 2009/0082270 A1   Mar. 26, 2009

Related U.S. Application Data

(60) Provisional application No. 60/873,933, filed on Dec. 8, 2006.

(51) Int. Cl.
C07K 14/00   (2006.01)
(52) U.S. Cl. .......................................... 514/2; 530/350
(58) Field of Classification Search .................. None
See application file for complete search history.

(56) References Cited

U.S. PATENT DOCUMENTS

| | | | |
|---|---|---|---|
| 5,935,852 A | 8/1999 | Follettie et al. | |
| 6,133,232 A | 10/2000 | De Robertis et al. | |
| 6,610,510 B1 | 8/2003 | Valenzuela et al. | |
| 7,316,998 B2 | 1/2008 | Knopf et al. | |
| 2002/0164682 A1 | 11/2002 | Follettie et al. | |
| 2003/0134790 A1 | 7/2003 | Langenfeld | |
| 2003/0194704 A1 | 10/2003 | Penn et al. | |
| 2003/0199042 A1 | 10/2003 | Valenzuela et al. | |
| 2004/0005560 A1 | 1/2004 | Isogai et al. | |
| 2004/0181033 A1 | 9/2004 | Han et al. | |
| 2005/0186663 A1 | 8/2005 | Davies et al. | |
| 2006/0105376 A1 | 5/2006 | Isogai et al. | |
| 2008/0032304 A1 | 2/2008 | Isogai et al. | |

FOREIGN PATENT DOCUMENTS

| EP | 1347046 | 9/2003 |
|---|---|---|
| WO | WO-97/48275 | 12/1997 |
| WO | WO-98/34951 | 8/1998 |
| WO | WO-98/49296 | 11/1998 |
| WO | WO-99/01553 | 1/1999 |
| WO | WO-99/40181 | 8/1999 |
| WO | WO-00/55193 | 9/2000 |
| WO | WO-02/10214 | 2/2002 |
| WO | WO-02/32929 | 4/2002 |
| WO | WO-02/054940 | 7/2002 |
| WO | WO-02/077204 | 10/2002 |
| WO | WO-02/078516 | 10/2002 |
| WO | WO-02/090992 | 11/2002 |
| WO | WO-03/055443 | 1/2003 |
| WO | WO-03/012082 | 2/2003 |
| WO | WO-03/055911 | 7/2003 |
| WO | WO-03/072714 | 9/2003 |
| WO | WO-03/106657 | 12/2003 |
| WO | WO-2004/074460 | 9/2004 |
| WO | WO-2005/003158 | 1/2005 |
| WO | WO-2005/115439 A2 | 12/2005 |

OTHER PUBLICATIONS

Avsian-Kretchmer et al., "Comparative geneomic analysisof the eight-membered ring cystine knot-containing bone morphogenetic protein antagonists," Molecular Endocrinology 18(1):1-12 (2004).
Belo et al., "Cerberus-like is a secreted factor with nerualizing activity expressed in the anterior primitive endoderm of the mouse gastrula," Mechanisims of Development 68:45-57 (1997).
Biben et al., "Murine Cerberus Homologue mCer-1: A canadidate anterior patterning molecule," Developmental Biology 194:135-151 (1998).
Bouwmeester et al., "Cerberus is a head-inducing secreted factor expressed in the anterior endoderm of Spemann's organizer," Nature 382:595-601 (1996).
Esteban et al., "The novel Cer-like protein Caronte mediates the extablishment of embryonic left-right asymmetry," Nature 401:243-251 (1999).
Katoh et al., "Identification and characterization of human CKTSF1B2 and CKTSF1B3 genes in silico," Oncology Reports 12:423-427 (2004).
Kuroda et al., "Neural Induction in Xenopus: requirement for extodermal and endomesodermal signals via chordin, noggin, β-catenin and cerberus," PLoS Biology 2(5):0623-0634 (2004).
Lah et al., "Human cerberus related gene CER1 maps to chromosome 9," Genomics 55:364-366 (1999).
Marques et al., "The activity of the nodal antagonist Cerl-2 in the mouse node is required for correct L/R body axis," Genes & Development 18:2342-2347 (2004).
Pearce et al., "A mouse cerberus/dan-related gene family," Developmental Biology 209:98-110 (1999).
Piccolo et al., "The head inducer Cerberus is a multifunctional antagonist of Nodal, BMP and Wnt signals," Nature 397:707-710 (1999).
Silva et al., "Endogenous Cerberus activity is required for anterior head specification in Xenopus," Development 130(20):4943-4953 (2003).
Stanley et al., "Murine cerberus homologue Cer1 maps to chromosome 4," Genomics 49:337-338 (1998).
Motoko Yanagita. BMP antagonists: Their roles in development and involvement in pathophysiology. Cytokine and Growth Factor Reviews. vol. 16, No. 3, pp. 309-319. 2005.
Brecher, A.S., et al., "Acetaldehyde Inhibits Chymotrypsin and Serum Anti-Chymotrypsin Activity," J. Investig Med., 46(4):146-152 (1998). Abstract only.
Livingston, S.F., et al., "The Significance of Chymotrypsin-Inhibitor Levels in the Serum of Patients with Carcinoma of the Breast," Cancer Research, 17(9):857-861 (1957).

*Primary Examiner*—Karen Cochrane Carlson
(74) *Attorney, Agent, or Firm*—Ropes & Gray LLP

(57) ABSTRACT

The disclosure relates to Cerberus/Coco polypeptides or variants thereof for use in treating a variety of disorders associated with myostatin, nodal and GDF-11.

6 Claims, 8 Drawing Sheets

US 7,833,971 B2

USES OF CERBERUS, COCO AND DERIVATIVES THEREOF

CROSS-REFERENCE TO RELATED AP antagonist protein that includes (at least) a myostatin binding domain of a Cerberus/Coco polypeptide or variant thereof. The myostatin antagonist protein binds to and neutralizes one or more of nodal and/or myostatin. Preferably, the pharmaceutical preparation is substantially free of pyrogenic materials so as to be suitable for administration as a human or veterinarian therapeutic.

Myostatin is widely recognized as an antagonist of muscle growth. Furthermore, myostatin null mice have shown resistance to obesity and diabetes under certain conditions. Therefore, the Cerberus/Coco proteins and pharmaceutical preparations described herein can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as age-related wasting, age-related frailty, cachexia, anorexia, Duchenne Muscular Dystrophy (DMD) syndrome, Becker's Muscular Dystrophy (BMD) syndrome, facio-scapular-humeral (FSH) muscular dystrophy, other muscular dystrophies, AIDS wasting syndrome, neuromuscular diseases, motor neuron diseases, diseases of the neuromuscular junction, and inflammatory myopathies. Excessive BMP4 activity has been associated with pathological ossification of various connective tissues. Therefore, the Cerberus/Coco proteins and pharmaceutical preparations that retain anti-BMP4 activity can be used to reduce the severity of a pathologic condition, which is characterized, at least in part, by an abnormal ossification in tissues such as muscles, tendons, and ligaments. BMP4 is also associated with Osteoarthritis (OA), including the development of osteophytes and synovial thickening; Fibrodysplasia ossificans progressiva (FOP); and atherosclerosis, especially inflammatory response in early steps of atherogenesis in lesion-prone areas; and craniosynostoses. Nodal signaling has been associated with certain cancers, particularly melanoma. Accordingly, Cerberus/Coco proteins and pharmaceutical preparations that retain anti-Nodal activity can be used to treat tumors, particularly tumors such as melanomas in which Nodal participates in tumor growth and development.

Another aspect of the invention provides a pharmaceutical preparation of Cerberus/Coco protein derivative for specifically inhibiting Nodal and/or myostatin function without substantially compromising BMP (such as BMP-4) signaling (e.g., does not substantially bind BMP-4 or other BMPs). Exemplary preparations of this aspect of the invention include polypeptides including the N-terminal truncated versions of Cerberus or Coco, or other fragments that include the cysteine-core. These so-called "N-terminally truncated Cerberus/Coco derivatives" can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

In certain embodiments, the mysotatin inhibitor is a polypeptide that includes a myostatin binding domain of a Cerberus/Coco protein. For instance, the Cerberus protein variant can be derived from a human, mouse, or other species of Cerberus, including a human or mouse Cerberus variant sequence sharing at least about 50%, 60%, 70%, 80%, 90%, 95%, or 99% or more sequence similarity or identity with the human or mouse Cerberus protein, and substantially retain the binding affinity of wild-type Cerberus for myostatin. Likewise, the Coco protein variant can be derived from a human, mouse, or other species of Coco, including a human or mouse Coco variant sequence sharing at least about 50%, 60%, 70%, 80%, 90%, 95%, or 99% or more sequence similarity or identity with the human or mouse Coco protein, and substantially retain the binding affinity of wild-type Coco for myostatin.

In certain related embodiments, the mysotatin inhibitor is a polypeptide that includes a myostatin binding domain of a Cerberus/Coco protein, which polypeptide does not substantially bind BMP-4 or BMP-2. For instance, the myostatin binding domain can be derived from a human, mouse, or other species of N-terminally truncated Cerberus, including a human or mouse Cerberus derivative, with amino acid residues starting from any one of residues 106-119 of SEQ ID No. 1 or 2, and ending at any residue after residue 241 of SEQ ID No. 1 or 2, preferably ending at any residue between residues 241 and 267 of SEQ ID No. 1 or 2 (all residue numbers inclusive).

For example, residues 106-119 of human Cerberus are:

```
PPGTQSLIQPIDGM         (SEQ ID NO: 7)
```

Residues 241-267 of human Cerberus are:

```
CKVKTEHEDGHILHAGSQDSFIPGVSA    (SEQ ID NO: 8)
```

Also included are Cerberus derived variant sequences, e.g., an N-terminally truncated myostatin binding domain of Cerberus that retains myostatin binding activity but loses other BMP binding activity. Variant sequences may be desirable as a way to alter selectivity of the inhibitor (e.g., relative to GDF-8, 11 or nodal binding), alter other binding characteristics with respect to myostatin (such as $K_d$, and/or $K_{on}$ or $K_{off}$ rates), or improve biodistribution or half life in vivo or on the shelf.

In certain preferred embodiments, the Cerberus polypeptide (full-length or N-terminally truncated) comprising the myostatin binding domain binds myostatin with a $K_d$ of 1 µM or less, and more preferably a $K_d$ of 100 nM, 10 nM or even 1 nM or less.

In certain related embodiments, the mysotatin inhibitor is a polypeptide that includes a myostatin binding domain of a Coco protein, such as the human Coco protein shown in SEQ ID NO:5 or in GenBank Accession number 22749329.

In certain preferred embodiments, the Coco polypeptide (full-length or N-terminally truncated) comprising the myostatin binding domain binds myostatin with a $K_d$ of 1 µM or less, and more preferably a $K_d$ of 100 nM, 10 nM or even 1 nM or less.

In certain embodiments, the Cerberus/Coco polypeptide (e.g., a myostatin binding domain thereof) is part of a fusion protein including, in addition to the myostatin binding domain, one or more polypeptide portions that enhance one or more of in vivo stability, in vivo half life, uptake/administration, tissue localization or distribution, formation of protein complexes, and/or purification. For instance, the fusion protein can include an immunoglobulin Fc domain. The fusion protein may include a purification subsequence, such as an epitope tag, a FLAG tag, a polyhistidine sequence, or as a GST fusion.

In certain embodiments, the Cerberus/Coco polypeptide (e.g., myostatin binding domain thereof) is part of a protein that includes one or more modified amino acid residues, such as a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

In certain embodiments, a subject variant Cerberus/Coco polypeptide is selective for binding and inhibition of myostatin, e.g., relative to 11 and/or nodal. For instance, the variant Cerberus/Coco polypeptide can be one which has a dissociation constant ($K_d$) for myostatin binding that is at least 2 times less than its $K_d$ for binding 11 and/or nodal, and even more preferably at least 5, 10, 100 or even 1000 times less. Whether by virtue of binding kinetics or biodistribution, the subject variant Cerberus/Coco polypeptide can also be selected based on relative in vivo potency, such as an inhibitor that has an $EC_{50}$ for inhibiting myostatin activity, or a particular physiological consequence (such as promoting muscle growth) that is at least 2 times less than its $EC_{50}$ for inhibiting 11 and/or nodal activities, and even more preferably at least 5, 10, 100 or even 1000 times less.

In certain embodiments, the subject variant Cerberus/Coco polypeptide is selective for binding and inhibition of myostatin, e.g., relative to other BMP proteins such as BMP4. For instance, the variant Cerberus/Coco polypeptide can be one which has a dissociation constant ($K_d$) for myostatin binding that is at least 2 times less than its $K_d$ for binding BMP4, and even more preferably at least 5, 10, 100 or even 1000 times less. Whether by virtue of binding kinetics or biodistribution, the subject variant Cerberus/Coco polypeptide can also be selected based on relative in vivo potency, such as an inhibitor that has an $EC_{50}$ for inhibiting myostatin activity, or a particular physiological consequence (such as promoting muscle growth) that is at least 2 times less than its $EC_{50}$ for inhibiting BMP4 activities, and even more preferably at least 5, 10, 100 or even 1000 times less.

In certain preferred embodiments, the variant Cerberus/Coco polypeptide binding domain binds myostatin with a $K_d$ of 1 μM or less, and more preferably a $K_d$ of 100 nM, 10 nM or even 1 nM or less.

In general, the subject myostatin inhibitor preparations are suitable for use in a human patients. In preferred embodiments, the subject preparations of variant Cerberus/Coco polypeptides will be substantially free of pyrogenic materials so as to be suitable for administration to a human patient.

In other embodiments, the subject variant Cerberus/Coco polypeptides can be administered to non-human animals, particularly other mammals. For example, the compounds of the present disclosure can be given to chickens, turkeys, livestock animals (such as sheep, pigs, horses, cattle, etc.), companion animals (e.g., cats and dogs) or may have utility in aquaculture to accelerate growth and improve the protein/fat ratio. To further illustrate, the subject variant Cerberus polypeptides can be used to stimulate growth or enhance feed efficiency of animals raised for meat production to improve carcass quality, or to increase milk production in dairy cattle.

Another aspect of the disclosure relates to packaged pharmaceuticals comprising a pharmaceutical preparation of a variant Cerberus/Coco polypeptide, as described herein, and a label or instructions for use in promoting growth of muscle tissue in a human patient.

Still another aspect of the disclosure relates to packaged pharmaceuticals comprising a pharmaceutical preparation of a variant Cerberus/Coco polypeptide, as described herein, and a label or instructions for veterinarian use in promoting growth of muscle tissue in a non-human mammal.

Another aspect of the disclosure relates to a method for inhibiting myostatin signal transduction in vivo by administering a pharmaceutical preparation of one or more of the subject variant Cerberus/Coco polypeptides. The subject method can be used to promote muscle growth, promote adipogenic differentiation, and/or promote bone growth or mineralization in human patients or in non-human animals.

In certain embodiments, the treatment methods of the present disclosure can be used to reduce the severity of a pathologic condition, which is characterized, at least in part, by an abnormal amount, development or metabolic activity of muscle or adipose tissue in a subject. For instance, the pharmaceutical preparations of the present disclosure can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD).

Exemplary motor neuron diseases that can be treated with a regimen including the subject myostatin include: Amyotrophic Lateral Sclerosis (ALS) (Also known as Lou Gehrig's Disease), Infantile Progressive Spinal Muscular Atrophy (SMA, SMA1 or WH) (Also known as SMA Type 1, Werdnig-Hoffman), Intermediate Spinal Muscular Atrophy (SMA or SMA2) (Also known as SMA Type 2), Juvenile Spinal Muscular Atrophy (SMA, SMA3 or KW) (Also known as SMA Type 3, Kugelberg-Welander), Spinal Bulbar Muscular Atrophy (SBMA) (Also known as Kennedy's Disease and X-Linked SBMA), and Adult Spinal Muscular Atrophy (SMA).

Exemplary inflammatory myopathies that can be treated with a regimen including the subject myostatin include: Dermatomyositis (PM/DM), Polymyositis (PM/DM), and Inclusion Body Myositis (IBM).

Exemplary diseases of the neuromuscular junction that can be treated with a regimen including the subject myostatin include: Myasthenia Gravis (MG), Lambert-Eaton Syndrome (LES), and Congenital Myasthenic Syndrome (CMS).

Exemplary myopathies due to endocrine abnormalities that can be treated with a regimen including the subject myostatin include: Hyperthyroid Myopathy (HYPTM) and Hypothyroid Myopathy (HYPOTM).

Exemplary diseases of peripheral nerve that can be treated with a regimen including the subject myostatin include: Charcot-Marie-Tooth Disease (CMT), Dejerine-Sottas Disease (DS), and Friedreich's Ataxia (FA).

Other exemplary myopathies that can be treated with a regimen including the subject myostatin include: Myotonia Congenita (MC), Paramyotonia Congenita (PC), Central Core Disease (CCD), Nemaline Myopathy (NM), Myotubular Myopathy (MTM or MM), and Periodic Paralysis (PP).

Exemplary metabolic diseases of muscle that can be treated with a regimen including the subject myostatin include: Phosphorylase Deficiency (MPD or PYGM), Acid Maltase Deficiency (AMD), Phosphofructokinase Deficiency (PFKM), Debrancher Enzyme Deficiency (DBD), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD).

The subject method can also be used to prevent, ameliorate or reduce the severity of a metabolic disorder, such as in the treatment of obesity or type II diabetes. To further illustrate, the subject variant Cerberus/Coco polypeptide preparations can be used to decrease body fat proportion in a subject.

In still other embodiments, the variant Cerberus/Coco polypeptide preparations can be used as part of such methods as reducing frailty associated with aging.

The subject pharmaceutical composition can also be used as myostatin antagonist to treat a number of neuronal system disease conditions, including CNS injuries/disease such as spinal cord injury and stroke, and PNS injuries/diseases.

In one aspect, the disclosure provides a myostatin antagonist protein comprising an amino acid sequence that is at least 90% identical to the sequence of amino acids 162-241 of human Cerberus (SEQ ID NO:2), and wherein said protein is substantially serum stable for a period of at least 24 hours.

In certain embodiments, the myostatin antagonist protein comprises an amino acid sequence that is at least 90%, 95%, 96%, 97%, 98%, 99%, or 100% identical to one or more of the following: the sequence of amino acids 156-241 of human Cerberus, the sequence of amino acids 156-267 of human Cerberus, the sequence of amino acids 141-241 of human Cerberus, the sequence of amino acids 141-267 of human Cerberus, the sequence of amino acids 119-241 of human Cerberus, the sequence of amino acids 41-241 of human Cerberus, the sequence of amino acids 41-267 of human Cerberus, the sequence of amino acids 18-241 of human Cerberus, or the sequence of amino acids 18-267 of human Cerberus.

In certain embodiments, the myostatin antagonist protein retains at least 50% of the myostatin antagonist activity after exposure to human serum for 24 hours at 37° C. The myostatin antagonist activity may be assessed, for example, in an A204 cell based assay.

In certain embodiments, the myostatin antagonist protein comprises a modification with respect to the amino acid sequence of SEQ ID NO:2 such that cleavage in human serum is reduced or eliminated. The modification with respect to the amino acid sequence of SEQ ID NO:2 may reduce or eliminate cleavage within one or more of the following sequences: the sequence SHCLPAK (SEQ ID NO: 22) of human Cerberus, the sequence MFRKTP (SEQ ID NO: 23) of human Cerberus, or the sequence NQRELP (SEQ ID NO: 24) of human Cerberus.

In another aspect, the disclosure provides a myostatin antagonist protein, the protein comprising an amino acid sequence that is at least 90% identical to the sequence of amino acids 101-185 of human Coco (SEQ ID NO:5), and wherein said protein is substantially serum stable for a period of at least 24 hours.

In certain embodiments, the myostatin antagonist protein comprises a modification with respect to the amino acid sequence of SEQ ID NO:5 such that cleavage in human serum is reduced or eliminated. The modification with respect to the amino acid sequence of SEQ ID NO:5 may reduce or eliminate cleavage within one or both of the following sequences: PARKRW (SEQ ID NO: 25) or SRRRVK (SEQ ID NO: 26) of human Coco.

In certain embodiments, the myostatin antagonist protein retains at least 50% of the myostatin antagonist activity after exposure to human serum for 24 hours at 37° C. The myostatin antagonist activity may be assessed, for example, in an A204 cell based assay.

In certain embodiments, the myostatin antagonist protein comprises a modification with respect to the amino acid sequence of SEQ ID NO:5 such that cleavage in human serum is reduced or eliminated. The modification with respect to the amino acid sequence of SEQ ID NO:5 may reduce or eliminate cleavage within one or both of the following sequences: PARKRW or SRRRVK of human Coco.

In certain embodiments, the myostatin antagonist protein may be a fusion protein including one additional polypeptide portion that enhances one or more of in vivo stability, in vivo half life, uptake/administration, tissue localization or distribution, formation of protein complexes, and/or purification. In certain embodiments, the fusion protein includes a portion of an immunoglobulin heavy chain constant domain. In certain embodiments, the fusion protein comprises an Fc domain of an immunoglobulin. In certain embodiments, the myostatin antagonist protein includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

In certain embodiments, the myostatin antagonist protein is a fusion protein that further comprises a second myostatin inhibitor domain, which is a polypeptide affinity reagent that selectively binds to myostatin and competes with the binding of an ALK7 or ALK4 receptor. In certain embodiments, the affinity reagent is one or more of the following: (i) an antibody agent, (ii) a peptide or scaffolded peptide that selectively binds to myostatin and competes with the binding of an ALK7 or ALK4 receptor, (iii) a myostatin binding domain of ALK7 or ALK4, or (iv) small organic molecule that selectively binds to myostatin and competes with the binding of an ALK7 or ALK4 receptor. Examples of suitable antibody agents include, for example, a recombinant antibody; a monoclonal antibody; a $V_H$ domain; a $V_L$ domain; an scFv; an Fab fragment; an Fab' fragment; an $F(ab')_2$; an Fv; or a disulfide linked Fv. In certain embodiments, the antibody agent is a fully human antibody or a humanized chimeric antibody, or an antigen binding fragment thereof.

In another aspect, the disclosure provides a pharmaceutical preparation comprising one or more of the myostatin antagonist proteins described herein.

In another aspect, the disclosure provides a method for inhibiting myostatin and/or GDF11 and/or Nodal in a patient, the method comprising administering to the patient an effective amount of one or more of the myostatin antagonist proteins described herein. In certain embodiments, inhibiting myostatin and/or GDF11 and/or Nodal in a patient causes a detectable change in the expression of a gene that is regulated by myostatin and/or GDF11 and/or Nodal.

In another aspect, the disclosure provides a method for increasing muscle mass in a patient, the method comprising administering to the patient an effective amount of one or more of the myostatin antagonist proteins described herein.

In another aspect, the disclosure provides a pharmaceutical preparation substantially free of pyrogenic materials, comprising a myostatin antagonist protein including a myostatin binding domain of a Cerberus or Coco polypeptide or variant thereof, which myostatin antagonist protein: (a) binds to and inhibits the signaling activity of one or more of Nodal, GDF11 and/or myostatin; and (b) does not substantially bind to BMP4.

In certain embodiments, the myostatin antagonist protein promotes growth of muscle tissue.

In certain embodiments, the myostatin binding domain has an amino acid sequence that is at least 90%, 95%, 96%, 97%, 98%, 99%, or 100% identical to one or both of the following: amino acids 162-241 of SEQ ID NO: 2, amino acids 101-189 of SEQ ID NO:5. In certain embodiments, the myostatin binding domain has an amino acid sequence that is at identical to an amino acid sequence selected from the group consisting of: amino acids 162-241 of SEQ ID NO: 2 and amino acids 101-189 of SEQ ID NO:5, or any naturally occurring human allelic variant thereof.

In certain embodiments, the myostatin antagonist protein does not include a full-length mature human Cerberus protein.

In certain embodiments, the myostatin antagonist protein is a fusion protein including one additional polypeptide portion that enhance one or more of in vivo stability, in vivo half life, uptake/administration, tissue localization or distribution, formation of protein complexes, and/or purification. In certain embodiments, the fusion protein includes a portion of an immunoglobulin heavy chain constant domain. In certain embodiments, the fusion protein comprises an Fc domain of an immunoglobulin.

In certain embodiments, the myostatin antagonist protein includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

In certain embodiments, the myostatin antagonist protein is a fusion protein that further comprises a second myostatin inhibitor domain, which is a polypeptide affinity reagent that selectively binds to myostatin and competes with the binding of an ALK7 or ALK4 receptor. In certain embodiments, the affinity reagent is one or more of the following: (i) an antibody agent, (ii) a peptide or scaffolded peptide that selectively binds to myostatin and competes with the binding of an ALK7 or ALK4 receptor, (iii) a myostatin binding domain of ALK7 or ALK4, or (iv) a small organic molecule that selectively binds to myostatin and competes with the binding of an ALK7 or ALK4 receptor. Examples of suitable antibody agents include, for example, a recombinant antibody; a monoclonal antibody; a $V_H$ domain; a $V_L$ domain; an scFv; an Fab fragment; an Fab' fragment; an $F(ab')_2$; an Fv; or a disulfide linked Fv. In certain embodiments, the antibody agent is a fully human antibody or a humanized chimeric antibody, or an antigen binding fragment thereof.

In another aspect, the disclosure provides a method for inhibiting myostatin and/or GDF11 in a patient, the method comprising administering to the patient an effective amount of a myostatin antagonist protein including a myostatin binding domain of a Cerberus or Coco polypeptide or variant thereof, which myostatin antagonist protein binds to and inhibits the signaling activity of one or more of nodal, GDF11 and/or myostatin. In certain embodiments, the myostatin binding domain has an amino acid sequence that is at least 90% identical to an amino acid sequence selected from the group consisting of: amino acids 162-241 of SEQ ID NO: 2 and amino acids 101-189 of SEQ ID NO:5. In certain embodiments, the myostatin binding domain has an amino acid sequence that is at identical to an amino acid sequence selected from the group consisting of: amino acids 162-241 of SEQ ID NO: 2 and amino acids 101-189 of SEQ ID NO:5, or any naturally occurring human allelic variant thereof. In certain embodiments, inhibiting myostatin and/or GDF11 in a patient causes a detectable change in the expression of a gene that is regulated by myostatin and/or GDF11. In certain embodiments, the myostatin antagonist does not substantially bind to BMP4.

In another aspect, the disclosure provides a method for increasing skeletal muscle mass in a patient in need thereof, the method comprising administering to the patient an effective amount of a myostatin antagonist protein including a myostatin binding domain of a Cerberus or Coco polypeptide or variant thereof, which myostatin antagonist protein binds to and inhibits the signaling activity of one or more of nodal, GDF11 and/or myostatin. In certain embodiments, the myostatin binding domain has an amino acid sequence that is at least 80% identical to an amino acid sequence selected from the group consisting of: amino acids 162-241 of SEQ ID NO: 2 and amino acids 101-189 of SEQ ID NO:5. In certain embodiments, the myostatin binding domain has an amino acid sequence that is at identical to an amino acid sequence selected from the group consisting of: amino acids 162-241 of SEQ ID NO: 2 and amino acids 101-189 of SEQ ID NO:5, or any naturally occurring human allelic variant thereof. In certain embodiments, the myostatin antagonist does not substantially bind to BMP4.

In another aspect, the disclosure provides use of a myostatin antagonist protein including a myostatin antagonist protein including a myostatin binding domain of a Cerberus or Coco polypeptide or variant thereof, which myostatin antagonist protein binds to and inhibits the signaling activity of one or more of nodal, GDF11 and/or myostatin for the preparation of a medicament for promoting growth of muscle tissue in a mammal.

DETAILED DESCRIPTION

I. Overview

Figure 1:
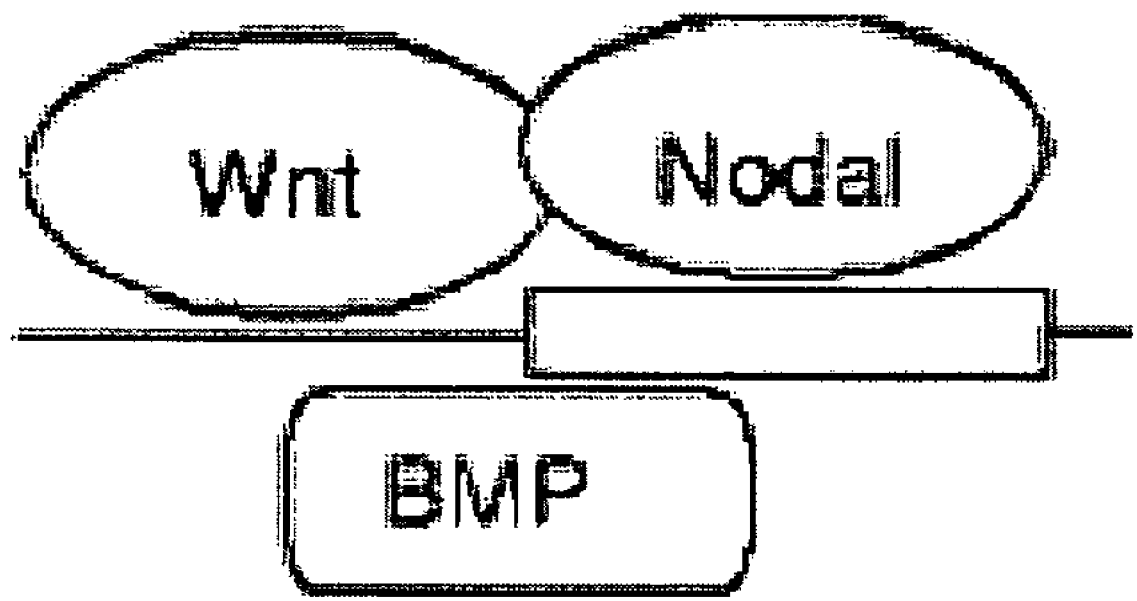
FIG. 1 shows a schematic drawing of where Wnt, Nodal and BMP bind to Cerberus. BMP-2 and the highly related BMP4 competitively bind Cerberus, likely in the same region. Other more distantly related or unrelated proteins, such as TGF-beta1, EGF, and PDGF, do not compete with BMP-4. The N-terminally truncated version of Cerberus still binds Xnr-1 (*Xenopus* homolog of mouse Nodal). (Adapted from Piccolo et al., Nature 397: 707-710, 1999).

Cerberus is expressed in the anterior endomesoderm (Bouwmeester et al., Nature 382: 595-601, 1996; Piccolo et al., Nature 397: 707-10, 1999; Rodriguez et al., Nature 401: 243-51, 1999) during development. Caronte, a chick ortholog, is involved in left-right asymmetry in the chick embryo (Rodriguez, supra). Cerberus functions as a multivalent growth factor antagonist in the extracellular space and inhibits signaling by BMP-4, nodal, and Wnt (Belo et al., Genesis 26: 265-70, 2000). Mouse Cerberus binds to BMP proteins and nodal via independent sites (Piccolo, supra), whereas the *Xenopus* Cerberus also binds Wnt proteins and inhibits their actions (Belo, supra). Cerberus has the unique property of inducing ectopic heads in the absence of trunk structures (Piccolo, supra). The expression of Cerberus during gastrulation is activated by nodal-related signals in endoderm and by Spemann-organizer factors (Yamamoto et al., Dev Biol 257: 190-204, 2003).

Orthologs for Cerberus can be found in *Xenopus tropicalis* and *Fugu rubripes*, but are missing in invertebrates. In *Fugu rubripes*, there is only one ortholog for Cerberus. All orthologous genes for Cerberus have two exons; the first eight amino acids of the cystine-knot domain are encoded by the 3' end of the first exon and the remainder of the motif by the second exon. In some orthologs, a predicted proteolytic cleavage site can be found upstream of the beginning of the cystine-knot domain.

Coco is another member of the Cerberus/Dan family of proteins that inhibits Nodal signaling.

In part, the present disclosure provides Coco or Cerberus derivatives for inhibiting Nodal, 11 and/or myostatin function. In certain embodiments, the Coco and Cerberus derivatives inhibit Nodal, 11 and/or myostatin function without substantially compromising BMP (such as BMP-4) signaling (e.g., does not substantially bind BMP-4 or other BMPs). The subject Cerberus derivatives may also be used to inhibit BMP (such as BMP-4) signaling.

Exemplary preparations of the subject disclosure include Cerberus polypeptide derivatives, including the N-terminal truncated versions of Cerberus or Coco. These so-called "Cerberus derivatives" or "Coco derivatives" can be used to reduce the severity of a pathologic condition, which is characterized, at least in part, by an abnormal amount, development or metabolic activity of muscle or adipose tissue in a subject. For instance, the pharmaceutical preparations of the present disclosure can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

II. Definitions

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope an meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the disclosure may include steps of comparing sequences to each other, including wild-type sequence to one or more mutants/sequence variants Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

A nucleic acid molecule is "hybridizable" to another nucleic acid molecule, such as a cDNA, genomic DNA, or RNA, when a single stranded form of the nucleic acid molecule can anneal to the other micleic acid molecule under the appropriate conditions of temperature and solution ionic strength (see Sambrook et al. *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS).

Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringency condition" is well understood in the art to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pages 9.47-9.57 of Sambrook, et al. (1989) *Molecular Cloning*, $2^{nd}$ ed., Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of micleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

"Polypeptide," "peptide" or "protein" are used interchangeably to describe a chain of amino acids that are linked together by chemical bonds called "peptide bonds." A protein or polypeptide, including an enzyme, may be a "native" or "wild-type," meaning that it occurs in nature; or it may be a "mutant," "variant," or "modified," meaning that it has been made, altered, derived, or is in some way different or changed from a native protein or from another mutant.

As used herein, the term "Cerberus/Coco protein" is used to signify the human Cerberus and Coco proteins, as well as homologs from other species (e.g., Caronte is the chicken Cerberus homolog) and derivatives (including forms with altered sequences and truncated forms) that retain a biological activity of the naturally occurring form.

"Cerberus or Cerberus-like protein" refers to mammalian Cerberus and Cerberus-like proteins, such as the murine (NCBI RefSeq ID NP_034017) or human (NCBI RefSeq ID NP_005445) Cerberus proteins (also see SEQ ID Nos. 2 and 8, respectively, of US 2002/0164682 A1, the entire contents of which is incorporated herein by reference), and other proteins which share sequence homology to the highly conserved cysteine pattern of the C-terminal portion of the mammalian Cerberus proteins. Exemplary amino acid sequences for Cerberus proteins include

```
Murine Cerberus protein (NCBI RefSeq ID NP_034017) (SEQ ID NO: 1):
  1  MHLLLVQLLV LLPLGKADLC VDGCQSQGSL SFPLLERGRR DLHVANHEEA EDKPDLFVAV

61  PHLMGTSLAG EGQRQRGKML SRLGRFWKKP ETEFYPPRDV ESDHVSSGMQ AVTQPADGRK

121  VERSPLQEEA KRFWERFMFR KGPAFQGVIL PIKSHEVHWE TCRTVPFNQT IAHEDCQKVV

181  VQNNLCFGKC SSIRFPGEGA DAHSFCSHCS PTKFTTVHLM LNCTSPTPVV KMVMQVEECQ

241  CMVKTERGEE RLLLAGSQGS FIPGLPASKT NP

Human Cerberus protein (NCBI RefSeq ID NP_005445) (SEQ ID NO: 2):
  1  MHLLLFQLLV LLPLGKTTRH QDGRQNQSSL SPVLLPRNQR ELPTGNHEEA EEKPDLFVAV

61  PHLVATSPAG EGQRQREKML SRFGRFWKKP EREMHPSRDS DSEPFPPGTQ SLIQPIDGMK

121  MEKSPLREEA KKFWHHFMFR KTPASQGVIL PIKSHEVHWE TCRTVPFSQT ITHEGCEKVV

181  VQNNLCFGKC GSVHFPGAAQ HSHTSCSHCL PAKFTTMHLP LNCTELSSVI KVVMLVEECQ

241  CKVKTEHEDG HILHAGSQDS FIPGVSA
```

The mouse and human Cerberus are as disclosed in US 2002/0164682 A1, as SEQ ID NOs. 1 and 7 (incorporated herein by reference).

NM_009887.1 (mouse Cerberus mRNA) (SEQ ID NO: 3).

```
   1 gggggggggg ggggtcagag ggagctttct tttaggcccg tccatctgtg aatctaacct 61 cagtttctgg gaatcaggaa gcatgcatct cctcttagtt cagctgcttg ttctcttgcc 121 tctggggaag gcagacctat gtgtggatgg ctgccagagt cagggctctt tatcctttcc 181 tctcctagaa aggggtcgca gagatctcca cgtggccaac cacgaggagg cagaagacaa 241 gccggatctg tttgtggccg tgccacacct catgggcacc agcctggctg ggaaggcca 301 gaggcagaga gggaagatgc tgtccaggct tggaagattc tggaagaaac ctgagaccga 361 attttacccc ccaagggatg tggaaagcga tcatgtctca tcggggatgc aggccgtgac 421 tcagccagca gatgggagga agtggagag atcacctcta caggaggaag ccaagaggtt 481 ctggcatcgg ttcatgttca gaaagggccc ggcgttccag ggagtcatcc tgcccatcaa 541 aagccacgaa gtacactggg agacctgcag gactgtgccc ttcaaccaga ccattgccca 601 tgaagactgt caaaaagtcg ttgtccagaa caacctttgc tttggcaaat gcagttccat 661 tcgttttccc ggagaagggg cagatgccca cagcttctgc tcccactgct cgcccaccaa 721 attcaccacc gtgcacttga tgctgaactg caccagccca accccgtgg tcaagatggt 781 gatgcaagta aagagtgtc agtgcatggt gaagacggaa cgtggagagg agcgcctcct 841 actggctggt tcccagggtt ccttcatccc tggacttcca gcttcaaaaa caaacccatg 901 aattacctca acagaaagca aaacctcaac agaataagtg agggttattc aatctggaaa 961 tgttatgtga gttatataaa gatcagtgga aaatatcttt ctctctccct ctctccccct 1021 ctctcttctc tctattttct ctctctctct ctctctctct ctctctctca 1081 cacacacaca cacacacaca cacacacaca catgtttgtg tttagacagg gtcttatgta 1141 ttctcagctg gcctcaaact cacaatgtgg ctggggatga ttttaaactc ctgatccaat 1201 tcctgagtgc tgggattaca gacatgctcc ataanacata gctcccagaa ggattttaa 1261 aagagatttt gcatgtttca aagttgcctt tgagactcag aaatattttg atntattgaa 1321 tggccttgcc acagatgtgg gaggcagctt gcttggtggc ccaagtattt tttttttgtt 1381 cgttcagaat tctccacatg aagtttttac tgttggttat ctggcgttga agaaggaata 1441 gtgaaggtac ttttaacagt ttacacgtgg aaggggctca ggcactagga accaaccttt 1501 tcccggaata tgaggaaaat acatgaacag tattagagtc acttgaggaa gttactagga 1561 aacgccataa gtctccaagt acattgtgag tcattttgaa ggacaatcgt gtatatagac 1621 gaaatcttct actcgtatgc ttttgaatct tctagcaagt taggtttcta tgtttgggct 1681 tcttcctatt gtctaagagt atgtgtgaca aattcaacct gacaaatacc tcaatggcaa 1741 attctgaccc tg
```

-continued

NCBI RefSeq ID NM_005454.1 (human Cerberus mRNA) (SEQ ID NO: 4).
```
  1 atgcatctcc tcttatttca gctgctggta ctcctgcctc taggaaagac cacacggcac 61 caggatggcc gccagaatca gagttctctt tcccccgtac tcctgccaag gaatcaaaga 121 gagcttccca caggcaacca tgaggaagct gaggagaagc cagatctgtt tgtcgcagtg 181 ccacaccttg tagccaccag ccctgcaggg gaaggccaga ggcagagaga gaagatgctg 241 tccagatttg gcaggttctg gaagaagcct gagagagaaa tgcatccatc cagggactca 301 gatagtgagc ccttcccacc tgggacccag tccctcatcc agccgataga tggaatgaaa 361 atggagaaat ctcctcttcg ggaagaagcc aagaaattct ggcaccactt catgttcaga 421 aaaactccgg cttctcaggg ggtcatcttg cccatcaaaa gccatgaagt acattgggag 481 acctgcagga cagtgccctt cagccagact ataacccacg aaggctgtga aaaagtagtt 541 gttcagaaca acctttgctt tgggaaatgc gggtctgttc attttcctgg agccgcgcag 601 cactcccata cctcctgctc tcactgtttg cctgccaagt tcaccacgat gcacttgcca 661 ctgaactgca ctgaactttc ctccgtgatc aaggtggtga tgctggtgga ggagtgccag 721 tgcaaggtga agacggagca tgaagatgga cacatcctac atgctggctc ccaggattcc 781 tttatcccag gagtttcagc ttga
```

It is also expected that Cerberus related proteins also exist in other species, including family members in *Xenopus*, and *Drosophila, C. elegans*, zebrafish, as well as in all mammals, for example, rats, mice and humans. "Cerberus or Cerberus-like proteins" also includes variants of the Cerberus proteins, such as allelic variants or variants induced by mutagenesis or deletions, and fragments of Cerberus proteins which variants and fragments retain myostatin binding activity. "Cerberus-like" proteins is also used to signify the family of proteins sharing structural and/or functional similarity, including those proteins which are described further herein. Such proteins may have amino acid sequences sharing significant sequence identity (e.g., at least about 50%, 60%, 70%, 80%, 90%, 95%, 99% or more) with the human or mouse Cerberus proteins, over the full-length, or at least within the myostatin binding domain of the human or mouse Cerberus. Cerberus-like proteins also include proteins that have amino acid sequences that are encoded by nucleic acid sequences that hybridize under stringent conditions with the coding sequences for human or mouse Cerberus, particularly that portion of the coding sequence for the myostatin binding domain. A Cerberus derivative or variant sequence may or may not lack the N-terminal BMP binding domain. A variety of allelic variants of human Cerberus are known, including A65G (alanine 65 to glycine), V179I and L221V.

"Coco or Coco-like protein" refers to mammalian Coco proteins and related homologs, such as the human Coco protein of GenBank Accession 22749329, and other proteins which share sequence homology to the highly conserved cysteine pattern of the C-terminal portion of the mammalian Coco proteins. An exemplary amino acid sequences for human Coco protein is (SEQ ID NO: 5)
```
  1  MLLGQLSTLL CLLSGALPTG SGRPEPQSPR PQSWAAANQT WALGPGALPP LVPASALGSW

61  KAFLGLQKAR QLGMGRLQRG QDEVAAVTLP LNPQEVIQGM CKAVPFVQVF SRPGCSAIRL

121  RNHLCFGNCS SLYIPGSDPT PLVLCNSCMP ARKRWAPVVL WCLTGSSASR RRVKISTMLI

181  EGCHCSPKA
```

Amino acids 1-21 of SEQ ID NO:5 correspond to a signal peptide that may be replaced with an alternative leader sequence. A mature secreted Coco polypeptide is expected to correspond to amino acids 22-189 of SEQ ID NO:5, although imprecisions in the signal peptide processing enzymes may lead to alternative or additional cleavage at positions ranging from one to five amino acids towards the amino terminus or the carboxy terminus from the glycine at position 22. As disclosed herein, a tPA leader sequence or other heterologous leader sequence may be used in place of the native leader sequence. Proposed leader sequences are as follows:

(i) Honey bee mellitin (HBML):
   MKFLVNVALVFMVVYISYIYA          (SEQ ID NO: 14)

(ii) Tissue Plasminogen Activator (TPA):
   MDAMKRGLCCVLLLCGAVFVSP         (SEQ ID NO: 15)

The human Coco coding sequence is disclosed in GenBank Accession 22749328 (incorporated herein by reference) (SEQ ID NO:6).

```
   1 agtccggaca gacagacagg cagacagacg cacggacaag cagatgctcc ttggccagct
  61 atccactctt ctgtgcctgc ttagcggggc cctgcctaca ggctcaggga ggcctgaacc
 121 ccagtctcct cgacctcagt cctgggctgc agccaatcag acctgggctc tgggcccagg
 181 ggccctgccc ccactggtgc cagcttctgc ccttgggagc tggaaggcct tcttgggcct
 241 gcagaaagcc aggcagctgg ggatgggcag gctgcagcgt gggcaagacg aggtggctgc
 301 tgtgactctg ccgctgaacc ctcaggaagt gatccagggg atgtgtaagg ctgtgccctt
 361 cgttcaggtg ttctcccggc ccggctgctc agccatacgc ctccgaaatc atctgtgctt
 421 tggtcattgc tcctctctct acatccctgg ctcggacccc accccactag tcctgtgcaa
 481 cagctgtatg cctgctcgca agcgttgggc acccgtggtc ctgtggtgtc tcactggcag
 541 ctcagcctcc cgtcgacggg tgaagatatc caccatgctg atcgaggggt gtcactgcag
 601 cccaaaagca tgaactgagc atcgtggatg ggtgcacgga gacacgcacc ttggagaaat
 661 gagggagat ggaccaagaa agacgtggac ctggatgatg tactctgggt caagagacca
 721 gggatgcagg gttaggcaga caggtcccca gagtcctcac cctgctcccc agacagtaga
 781 cacagtgccc gtcctggagt tgcaccactg atagtcacag cacacaatga ttgacaactc
 841 acttttttt ttttttttga gatggagtct cgctctgtcg cccaggctgg agtgcagtgg
 901 cgcaatctca gctcactgca agctccacct cccgggttta tgccattctc ctgtctcagc
 961 ctcccgagta gctgggacta caggcacccg ccaacacgcc cggctaattt ttcgtatttt
1021 tagtaaagac agggtttcac cgtgttagcc aggatggtct ctatctcctg acctcgtgat
1081 ctgcctgcct tggccttatt attttttttt tttaaggaca gagtctctct ctgtcaccca
1141 ggctggagtg caatggcgcg atcttggctc actgtaactt ccacttgcca ggctcaagca
1201 gttctcctgc ctcagcctcc tgagtagctg ggactacagg cacccgccac catgcccagc
1261 taattttgt atttttagta gagacagagt ttcaccatat tagcctggct ggtctcaaac
1321 tcctggcctc aggtgatctg cccacctcgg cctcccaaag tgctgggatc aaatccactg
1381 ttaatcatta ggctgaactg tctcttatag aatgaggtca aagacactcc cagttgcagg
1441 gagggtagat ggcccccaccc agaccgagag acacagtgat gacctcagcc tagggacacc
1501 aaaaaaaaaa aaaaaaaaa cccaaaccaa aaacgcaaac caaagcaggc aggcagacag
1561 ctgctggggg aaatcctggg gtccttgaga cagaggcagg accctcgtgt tcccagctgc
1621 ctcttgcctt gatagtggtg ctgtgtccct ctcagacccc ccacctgagt ctccacagag
1681 ccccacgcct ggcatggcat tccacagaaa ccataaaggt tggctgagtc c
```

It is also expected that Coco-related proteins also exist in other species, including family members in *Xenopus*, and *Drosophila*, *C. elegans*, zebrafish, as well as in all mammals, for example, rats, mice and non-human primates. "Coco or Coco-like proteins" also includes variants of the naturally occurring Coco proteins, such as allelic variants or variants induced by mutagenesis or deletions, and fragments of Coco proteins which variants and fragments retain myostatin binding activity. "Coco-like" proteins is also used to signify the family of proteins sharing structural and/or functional similarity, including those proteins which are described further herein. Such proteins may have amino acid sequences sharing significant sequence identity (e.g., at least about 50%, 60%, 70%, 80%, 90%, 95%, 99% or more) with the human Coco protein, over the full-length, or at least within the myostatin binding domain of the human Coco. Coco-like proteins also include proteins that have amino acid sequences that are encoded by nucleic acid sequences that hybridize under stringent conditions with the coding sequences for human Coco, particularly that portion of the coding sequence for the myostatin binding domain. A Coco derivative or variant sequence may or may not lack the N-terminal BMP binding domain.

Unless specifically stated otherwise, "Cerberus (derivative) therapeutics" or its grammatical variations include the full-length or the N-terminally truncated versions of Cerberus therapeutics.

As used herein, the term "Cerberus or Cerberus-like activity" refers to one or more of the activities which are exhibited by the mammalian Cerberus-like proteins of the present disclosure. In particular, "Cerberus or Cerberus-like activity" includes the ability to induce, enhance and/or inhibit the formation, growth, proliferation, differentiation, maintenance of neurons and/or related neural cells and tissues such as brain cells, Schwann cells, glial cells and astrocytes. "Cerberus or Cerberus-like" activity also includes the ability to induce molecular markers of neuroendocrine or ectoderm tissue, such as OTX2, N-CAM, MASH, chromagranin, and AP2, as well as the ability to induce the formation of neurons and/or related neural cells and tissues such as brain cells, Schwann cells, glial cells and astrocytes. "Cerberus or Cerberus-like activity" may also include the ability to regulate the interaction of ligands and their protein receptors. "Cerberus or Cerberus-like activity" may further include the ability to regulate the formation, differentiation, proliferation and/or maintenance of other cells and/or tissue, for example connective tissue, organs and wound healing. In particular, "Cerberus or Cerberus-like activity" may include the ability to enhance and/or inhibit the formation, growth, proliferation, differentiation and/or maintenance of cardiac, spleen, liver, pancreas, stomach, kidney, lung and brain cells and tissue, as well as osteoblasts and bone, chondrocytes and cartilage, tendon, epidermis and muscle. "Cerberus and Cerberus-like activity" also includes the activities of Cerberus and Cerberus-like protein in the assays described in the examples and specification herein.

Cerberus and Cerberus-like nucleotide sequences in mouse and human are as disclosed in US 2002/0164682 A1, as SEQ ID NOs. 1 and 7 (incorporated herein by reference). Also see NCBI RefSeq ID NM_005454.1 (human) and NM_009887.1 (mouse).

In certain related embodiments, the mysotatin inhibitor is a polypeptide that includes a myostatin binding domain of a Coco protein, such as the human Coco protein.

The terms "antibody" and "antibody agent" are used interchangeably herein, and refer to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG).

The term "antigen binding fragment" includes any portion of an antibody that binds to a target epitope. An antigen binding fragment may be, for example, a polypeptide including a CDR3 region, or other fragment of an immunoglobulin molecule which retains the affinity and specificity of the myostatin epitope.

"Specifically binds" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between the subject myostatin neutralizing antibodies and a other proteins. Nevertheless, specific binding, may be distinguished as mediated through specific recognition of the myostatin protein. Typically specific binding results in a much stronger association between the antibody and myostatin protein than between the antibody and other proteins, e.g., GDF11. Specific binding by an antibody to myostatin under such conditions requires an antibody that is selected for its specificity for a particular protein. The affinity constant (Ka, as opposed to Kd) of the antibody binding site for its cognate monovalent antigen is at least $10^7$, usually at least $10^8$, preferably at least $10^9$, more preferably at least $10^{10}$, and most preferably at least $10^{11}$M. A variety of immunoassay formats are appropriate for selecting antibodies specifically reactive with myostatin. For example, solid-phase ELISA immunoassays are routinely used to select monoclonal antibodies specifically reactive with a protein. See Harlow and Lane (1988) Antibodies, A Laboratory Manual, Cold Spring Harbor Publications, New York, for a description of immunoassay formats and conditions that can be used to determine specific reactivity.

Immunoassays in the competitive binding format can be used to determine cross-reactivity of antibodies with myostatin, e.g., to identify whether a test antibody is a myostatin neutralizing antibody. For example, the myostatin protein, or a fragment thereof is immobilized to a solid support. Test antibodies are added to the assay compete with the binding of a TGF receptor, such as ActRII or ALK7, to the immobilized antigen. The ability of the test antibodies to compete with the binding of a TGF receptor to the immobilized myostatin antigen is compared.

Similarly, immunoassays in the competitive binding format can be used to determine cross-reactivity determinations, e.g., to determine the specificity of a myostatin neutralizing antibody. For example, the myostatin protein, or the myostatin epitope thereof is immobilized to a solid support. Epitopes from other proteins, such as 11, Nodal or BMP-4 or other proteins having sequence homology with myostatin are added to the assay to compete with the binding of a potential myostatin neutralizing antibody to the immobilized antigen. The ability of the test peptides to compete with the binding of potential myostatin neutralizing antibody with the immobilized myostatin antigen is compared. The percent cross-reactivity of the potential myostatin neutralizing antibody for the other antigens is calculated, using standard calculations. In certain preferred embodiments, the subject myostatin neutralizing antibodies have less than 10% cross-reactivity with 11. In other preferred embodiments, the subject myostatin neutralizing antibodies have less than 1%, 5%, or 10% cross-reactivity with BMP-4.

III. Exemplary Cerberus and Coco Derivatives

In certain embodiments, the mysotatin inhibitor is a Cerberus polypeptide sharing at least about 50%, 60%, 70%, 80%, 90%, 95%, 99% or more sequence identity over the full-length of the human or mouse Cerberus protein.

In certain other embodiments, the mysotatin inhibitor is a polypeptide that includes a Cerberus sequence obtained from human, mouse, or other species, their variants or derivatives, including N-terminally truncated versions of Cerberus. The full-length mouse and human Cerberus proteins, disclosed as SEQ ID NOs. 2 and 8, respectively, in US 2002/0164682 A1, are also disclosed in NCBI RefSeq format below:

```
Human Cerberus full length protein (SEQ ID NO: 2):
  1 MHLLLFQLLV LLPLGKTTRH QDGRQNQSSL SPVLLPRNQR ELPTGNHEEA EEKPDLFVAV 61 PHLVATSPAG EGQRQREKML SRFGRFWKKP EREMHPSRDS DSEPFPPGTQ SLIQPIDGMK
121 MEKSPLREEA KKFWHHFMFR KTPASQGVIL PIKSHEVHWE TCRTVPFSQT ITHEGCEKVV
181 VQNNLCFGKC GSVHFPGAAQ HSHTSCSHCL PAKFTTMHLP LNCTELSSVI KVVMLVEECQ

241 CKVKTEHEDG HILHAGSQDS FIPGVSA
```

Residues 106-119 (from any one of which residues the subject Cerberus derivatives may begin), and residues 241-267 (to any one of which residues the subject Cerberus derivatives may end) are underlined.

```
Mouse Cerberus full length protein (SEQ ID NO: 1):
  1 MHLLLVQLLV LLPLGKADLC VDGCQSQGSL SFPLLERGRR DLHVANHEEA EDKPDLFVAV

61 PHLNGTSLAG EGQRQRGKML SRLGRFWKKP ETEFYPPRDV ESDHVSSGMQ AVTQPADGRK

121 VERSPLQEEA KRFWHRFMFR KGPAFQGVIL PIKSHEVHWE TCRTVPFNQT IAHEDCQKVV

181 VQNNLCFGKC SSIRFPGEGA DAHSFCSHCS PTKFTTVHLM LNCTSPTPVV KMVMQVEECQ

241 CMVKTERGEE RLLLAGSQGS FIPGLPASKT NP
```

Residues 106-119 (from any one of which residues the subject Cerberus derivatives may begin), and residues 241-272 (to any one of which residues the subject Cerberus derivatives may end) are underlined. Note that the mouse protein is largely homologous to the human protein throughout the sequences, with the exception of 5 additional residues at the C-terminus. Therefore, whenever a non-human Cerberus derivative is used, the residue numbers refers to those corresponding to the human sequences.

As described above, in certain embodiments, preferred fragments of the human Cerberus derivative proteins are ones which begins anywhere from residues 106-119 (inclusive) at the N-terminus, and ends anywhere after residue 241. A variety of additional Cerberus and Coco derivatives and variants are described in the Examples.

Also included are Cerberus derived variant sequence, including mutants or variants of the wild-type myostatin binding domains that retain myostatin binding activity, optionally substantially loses BMP-4 binding. Variant sequences without BMP binding affinity may be desirable as a way to alter selectivity of the inhibitor (e.g., relative to 11 or nodal binding, where preferential binding to one of the proteins occur. Also includes more preferential—higher affinity than wild-type—binding to myostatin, or more discrimitory—lower affinity than wild-type truncated version—binding to BMP-4), alter other binding characteristics with respect to myostatin (such as $K_d$, and/or $K_{on}$ or $K_{off}$ rates), or improve biodistribution or half life in vivo or on the shelf.

Certain other Cerberus sequences are listed below based on homology search in databases of identified proteins, and the subject variant Cerberus polypeptides can be derived from those proteins as well. Since these sequences are retrieved from public databases available on the internet, additional homologs of the proteins in other species may be obtained as these databases are being updated. Furthermore, other species of Cerberus proteins, especially those of mammals, can be readily obtained by standard molecular biology protocols, such as PCR, low stringency hybridization, Ab-mediated screening of expression libraries using antibodies cross-reacting with identified Cerberus homologs in target species, etc.

For example, sequence alignments using softwares such as DNAStar's MegaAlign (supra) can identify the most conserved regions in the known members of a protein family. PCR can then be carried out using degenerate oligoes covering such most conserved regions, and templates DNA from the target organism. In preferred embodiments, such conserved regions include the kinase domain, and/or the ligand binding domain.

These same conserved regions may be used to generate probes for screening nucleic acid libraries at moderate to low stringency hybridization conditions (see definition section).

In certain embodiments, the mysotatin inhibitor is a Cerberus polypeptide sharing at least about 50%, 60%, 70%, 80%, 90%, 95%, 99% or more sequence identity over the full-length of the human or mouse Cerberus protein.

In certain other embodiments, the mysotatin inhibitor is a polypeptide that includes a Coco sequence obtained from human, mouse, or other species, their variants or derivatives, including N-terminally truncated versions of Coco. The full-length human Coco protein is disclosed above.

The various Cerberus and Coco polypeptides may be prepared as fusion proteins. A fusion protein may include one or more additional polypeptide portion that enhance one or more of in vivo stability, in vivo half life, uptake/administration, tissue localization or distribution, formation of protein complexes, and/or purification. For example, a fusion protein may include a portion of a constant region of a immunoglobulin heavy chains, e.g., an immunoglobulin Fc domain, and/or a purification subsequence selected from: an epitope tag, a FLAG tag, a polyhistidine sequence, and a GST fusion. The myostatin antagonist protein may include one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

A fusion protein or coupled protein system (e.g. non-fusion covalent linkage by crosslinking) may also include a second myostatin inhibitor domain, which is a polypeptide affinity reagent that selectively binds to myostatin and competes with the binding of an ALK7 or ALK4 receptor. The affinity reagent may be an antibody agent. An antibody agent may be, for example, a recombinant antibody; a monoclonal antibody; a VH domain; a VL domain; an scFv; an Fab fragment; an Fab' fragment; an F(ab')2; an Fv; or a disulfide linked Fv, a fully human antibody or a humanized chimeric antibody, or an antigen binding fragment thereof. An affinity reagent is a peptide or scaffolded peptide that selectively binds to myostatin and competes with the binding of an ALK7 or ALK4 receptor. An affinity reagent may include a myostatin binding domain of ALK7 or ALK4. For example, an extracellular domain of ALK7 or ALK4 (preferably human ALK7 or ALK4) may be used. The affinity reagent may be a small organic molecule that selectively binds to myostatin and competes with the binding of an ALK7 or ALK4 receptor.

An example of a human ALK7 myostatin binding domain is shown below:

(SEQ ID NO: 9)
LKCVCLLCDSSNFTCQTEGACWASVMLTNGKEQVIKSCVSLPELNAQVFC

HSSNNVTKTECCFTDFCNNITLHLP

An example of a human ALK4 myostatin binding domain is shown below:

(SEQ ID NO: 10)
ALLCACTSCLQANYTCETDGACMVSIFNLDGMEHHVRTCIPKVELVPAGK

PFYCLSSEDLRNTHCCYTDY

As shown herein, Caronte, the chicken ortholog of Cerberus does not substantially inhibit Activin A signaling in an A204 Reporter Gene Assay. Similarly, we have determined that human Cerberus and Coco do not inhibit Activin A. Thus, such myostatin antagonists will preferably exhibit little or no interaction with Activin A-mediated signaling.

IV. Exemplary Therapeutic Uses

The subject Coco and Cerberus polypeptides, such as the full-length and the N-terminally truncated Cerberus derivatives or Coco derivatives, can be used in a number of therapeutic settings to treat a number of diseases resulting from or exacerbated by the presence of myostatin. Decreased myostatin expression or activity has been shown to be beneficial for promoting muscle growth, inhibiting fat accumulation and normalizing glucose homeostasis in the context of models of diabetes.

In certain embodiments, the subject polypeptides and derivatives thereof are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

In DMD, boys begin to show signs of muscle weakness as early as age 3. The disease gradually weakens the skeletal or voluntary muscles, those in the arms, legs and trunk. By the early teens or even earlier, the boy's heart and respiratory muscles may also be affected. BMD is a much milder version of DMD. Its onset is usually in the teens or early adulthood, and the course is slower and far less predictable than that of DMD. (Though DMD and BMD affect boys almost exclusively, in rare cases they can affect girls.

Until the 1980s, little was known about the cause of any kind of muscular dystrophy. In 1986, the dystrophin gene deficiency was identified as the cause of DMD. BMD results from different mutations in the same gene. BMD patients have some dystrophin, but it's either insufficient in quantity or poor in quality. Having some dystrophin protects the muscles of those with BMD from degenerating as badly or as quickly as those of people with DMD.

Recent researches demonstrate that blocking or eliminating Myostatin function in vivo can effectively treat at least certain symptoms in DMD and BMD patients (Bogdanovich et al., supra; Wagner et al., supra). Thus, the subject Cerberus derivatives, especially the N-terminally truncated versions thereof, constitute an alternative means of blocking the function of Myostatin in vivo in DMD and BMD patients.

Similarly, the subject Coco or Cerberus derivatives, especially the N-terminally truncated versions thereof, provide an effective means to increase muscle mass in other disease conditions that are in need of muscle growth. For example, Gonzalez-Cadavid et al. (supra) reported that that Myostatin expression correlates inversely with fat-free mass in humans and that increased expression of the Myostatin gene is associated with weight loss in men with AIDS wasting syndrome. By inhibiting the function of Myostatin in AIDS patients, at least certain symptoms of AIDS may be alleviated, if not completely eliminated, thus significantly improving quality of life in AIDS patients.

Since loss of Myostatin function is also associated with fat loss without diminution of nutrient intake (Zimmers et al., supra; McPherron and Lee, supra), the subject Coco or Cerberus derivatives, especially the N-terminally truncated versions thereof, may further be used as a therapeutic agent for slowing or preventing the development of obesity and type II diabetes.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process.

Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of Myostatin in adult mice was found to induce profound muscle and fat loss analogous to that seen in human cachexia syndromes (Zimmers et al., supra), the subject Coco or Cerberus derivatives, especially the N-terminally truncated versions thereof as a pharmaceutical composition can be beneficially used as a Myostatin antagonist/blocker to prevent, treat, or alleviate the symptoms of the cachexia syndrome, where muscle growth is desired.

In certain embodiments, the subject variant Coco or Cerberus polypeptides, particularly the N-terminally truncated Cerberus derivatives, can be used to form pharmaceutical compositions that can be beneficially used to prevent, treat, or alleviate symptoms of a host of diseases involving neurodegeneration. While not wishing to be bound by any particular theory, the subject Cerberus derivatives may antagonize the inhibitory feedback mechanism mediated through the wild-type ALK7 receptor, thus allowing new neuronal growth and differentiation. The subject Cerberus derivative as a pharmaceutical composition can be beneficially used to prevent, treat, or alleviate symptoms of diseases with neurodegeneration, including Alzheimer's Disease (AD), Parkinson's Disease (PD), Amyotrophic Lateral Sclerosis (ALS), Huntington's disease, etc.

Alzheimer's disease (AD) is a chronic, incurable, and unstoppable central nervous system (CNS) disorder that occurs gradually, resulting in memory loss, unusual behavior, personality changes, and a decline in thinking abilities. These losses are related to the death of specific types of brain cells and the breakdown of connections between them.

AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses. AD patients most commonly die from pneumonia, 8 to 20 years from disease onset.

Parkinson's disease (PD) is a chronic, incurable, and unstoppable CNS disorder that occurs gradually and results in uncontrolled body movements, rigidity, tremor, and gait difficulties. These motor system problems are related to the death of brain cells in an area of the brain that produces dopamine—a chemical that helps control muscle activity.

In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden. People with PD usually die from pneumonia.

Amyotrophic lateral sclerosis (ALS; Lou Gehrig's disease; motor neuron disease) is a chronic, incurable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles.

Most people are diagnosed with ALS between 40 and 70 years of age. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

The causes of these neurological diseases has remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

Huntington's disease (HD) is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing. The rate of disease progression and the age of onset vary from person to person.

Tay-Sachs disease and Sandhoff disease are glycolipid storage diseases caused by the lack of lysosomal β-hexosaminidase (Gravel et al., in *The Metabolic Basis of Inherited Disease*, eds. Scriver et al., McGraw-Hill, New York, pp. 2839-2879, 1995). In both disorders, $G_{M2}$ ganglioside and related glycolipid substrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., *Hum. Mol. Genet.* 6: 1879-1885, 1997).

It is well-known that apoptosis plays a role in AIDS pathogenesis in the immune system. However, HIV-1 also induces neurological disease. Shi et al. (*J. Clin. Invest.* 98: 1979-1990, 1996) examined apoptosis induced by HIV-1 infection of the central nervous system (CNS) in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is a also a salient feature of prion diseases, such as Creutzfeldt-Jakob disease in human, BSE in cattle (mad cow disease), Scrapie Disease in sheep and goats, and feline spongiform encephalopathy (FSE) in cats.

The subject Cerberus and Coco polypeptides, including the N-terminally truncated Cerberus derivatives are also useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term peripheral neuropathy encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium *Mycobacterium leprae*, which attacks the peripheral nerves of affected people. According to statistics gathered by the World Health Organization, an estimated 1.15 million people have leprosy worldwide.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic—no known cause can be found. The most common of the inherited peripheral neuropathies in the United States is Charcot-Marie-Tooth disease, which affects approximately 125,000 persons.

Another of the better known peripheral neuropathies is Guillain-Barré syndrome, which arises from complications associated with viral illnesses, such as cytomegalovirus, Epstein-Barr virus, and human immunodeficiency virus (HIV), or bacterial infection, including *Campylobacter jejuni* and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the peripheral nervous system (PNS) and the central nervous system (CNS), as well as other body tissues.

Other PNS diseases treatable with the subject Cerberus and Coco polypeptides include: Brachial Plexus Neuropathies (Diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al. Principles of Neurology, $6^{th}$ ed, pp 1351-2); Diabetic Neuropathies (Peripheral, autonomic, and cranial nerve disorders that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy. See Adams et al., Principles of Neurology, $6^{th}$ ed, p 1325); Mononeuropathies (Disease or trauma involving a single peripheral nerve in isolation, or out of proportion to evidence of diffuse peripheral nerve dysfunction. Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions); Neuralgia (Intense or aching pain that occurs along the course or distribution of a peripheral or cranial nerve); Peripheral Nervous System Neoplasms (Neoplasms which arise from peripheral nerve tissue. This includes neurofibromas; Schwannomas; granular cell tumors; and malignant peripheral nerve sheath tumors. See DeVita Jr et al., Cancer: Principles and Practice of Oncology, $5^{th}$ ed, pp 1750-1); Nerve Compression Syndromes (Mechanical compression of nerves or nerve roots from internal or external causes. These may result in a conduction block to nerve impulses, due to, for example, myelin sheath dysfunction, or axonal loss. The nerve and nerve sheath injuries may be caused by ischemia; inflammation; or a direct mechanical effect); Neuritis (A general term indicating inflammation of a peripheral or cranial nerve. Clinical manifestation may include pain; paresthesias; paresis; or hyperthesia); Polyneuropathies (Diseases of multiple peripheral nerves. The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance).

In certain embodiments, the subject full-length Coco or Cerberus polypeptides or variants thereof are used as part of a treatment for diseases or conditions characterized by excessive or undesirable levels of BMP, such as the ones described below.

The heterotopic ossification of muscles, tendons, and ligaments is a common problem faced by orthopaedic surgeons. Hannallah et al. (J Bone Joint Surg Am. 2004 January; 86-A (1):80-91) investigated the ability of Noggin (a BMP [bone morphogenetic protein] antagonist) to inhibit heterotopic ossification. Three varying doses of Noggin-expressing muscle-derived stem cells inhibited the heterotopic ossification elicited by BMP-4-expressing muscle-derived stem cells. Each of three varying doses of Noggin-expressing muscle-derived stem cells also significantly inhibited the heterotopic ossification elicited by demineralized bone matrix. All eleven animals that underwent Achilles tenotomy developed heterotopic ossification at the site of the injury in the control limbs. In contrast, the limbs treated with the Noggin-expressing muscle-derived stem cells had a reduction in the formation of heterotopic ossification of 83% and eight of the eleven animals had no radiographic evidence of heterotopic ossification (p<0.05). Thus, delivery of Noggin mediated by muscle-derived stem cells can inhibit heterotopic ossification caused by BMP4, demineralized bone matrix, and trauma in an animal model, indicating that gene therapy to deliver BMP inhibitors (Noggin or Cerberus) may become a powerful method to inhibit heterotopic ossification in targeted areas of the body. See also Glaser et al. (J Bone Joint Surg Am. 2003 December; 85-A(12):2332-42).

Osteoarthritis (OA) is a joint disease characterized by osteophyte development, fibrosis, and articular cartilage damage. Effects of exogenous transforming growth factor beta (TGFbeta) isoforms and bone morphogenetic proteins (BMPs) suggest a role for these growth factors in the pathogenesis of OA. Scharstuhl et al. (Arthritis Rheum. 2003 December; 48(12):3442-51) used adenoviral overexpression of TGF-beta and BMP antagonists to block the signaling of TGF-beta and BMP. The inhibitors studied include a secreted, pan-specific TGF-beta antagonist called murine latency-associated peptide 1 (mLAP-1), intracellular inhibitory Smad6

(a BMP antagonist), and Smad7 (a TGF-beta/BMP inhibitor). Intraarticular injection of papain caused increased protein expression of several TGF-beta and BMP isoforms in synovium and cartilage. Adenovirus transfection into the joint resulted in a strong expression of the transgenes in the synovial lining. Overexpression of mLAP-1, Smad6, and Smad7 led to a significant reduction in osteophyte formation compared with that in controls. Smad6 and Smad7 overexpression also significantly decreased synovial thickening. Furthermore, the secreted TGF-beta inhibitor mLAP-1 increased articular cartilage PG loss. These results indicate a pivotal role of excessive endogenous TGF-beta and BMP in the development of osteophytes and synovial thickening, implicating excessive endogenous TGFbeta and BMP in the pathogenesis of OA. In contrast, the prevention of cartilage damage by endogenous TGF-beta signifies the protective role of TGF-beta in articular cartilage. Thus the subject Coco or Cerberus pharmaceutical compositions can be used as BMP antagonists to treat OA, including the development of osteophytes and synovial thickening.

In an analysis of normal ovarian surface epithelium (OSE) and ovarian cancer (OC) cells, Shepherd and Nachtigal (Endocrinology. 2003 August; 144(8):3306-14) observed BMP4 mRNA expression and found that primary OC cells produce mature BMP4. In addition, each member of the downstream signaling pathway was expressed in primary OSE and OC cells. Smad1 was phosphorylated and underwent nuclear translocation in normal OSE and OC cells upon treatment with BMP4. Interestingly, the BMP target genes ID1 and ID3 were up-regulated 10- to 15-fold in primary OC cells, compared with a 2- to 3-fold increase in normal OSE. The growth of several primary OC cells was relatively unaltered by BMP4 treatment; however, long-term BMP4 treatment of primary OC cells resulted in decreased cell density as well as increased cell spreading and adherence. These data demonstrate the existence and putative function of BMP signaling in normal OSE and OC cells, and thus the subject Cerberus pharmaceutical preparations can be used to regulate BMP4 signaling in OC pathogenesis.

Fibrodysplasia ossificans progressiva (FOP), a rare genetic disabling disease characterized by heterotopic bone formation, is of special interest for general medicine since the bone morphogenetic proteins (especially BMP4 involved in its pathogenesis are known to play a role in skeletal morphogenesis, and the gene antagonist to BMP-4 (such as noggin) might be useful in preventing lamellar bone formation. See Blaszczyk et al. (Eur J. Dermatol. 2003 May-June; 13(3):234-7). Thus the subject Cerberus therapeutics may also be used to treat FOP.

Atherosclerosis is now viewed as an inflammatory disease occurring preferentially in arterial regions exposed to disturbed flow conditions, including oscillatory shear stress (OS), in branched arteries. Sorescu et al. (J Biol Chem. 278 (33):31128-35, 2003) suggest that BMP4 is a mechanosensitive, inflammatory factor playing a critical role in early steps of atherogenesis in the lesion-prone areas. Thus the subject Cerberus therapeutics may be used to control BMP-4 induced inflammatory response in early steps of atherogenesis in those areas.

During skull development, the cranial connective tissue framework undergoes intramembranous ossification to form skull bones (calvaria). As the calvarial bones advance to envelop the brain, fibrous sutures form between the calvarial plates. Expansion of the brain is coupled with calvarial growth through a series of tissue interactions within the cranial suture complex. Craniosynostosis, or premature cranial suture fusion, results in an abnormal skull shape, blindness and mental retardation. Recent studies have demonstrated that gain-of-function mutations in fibroblast growth factor receptors (fgfr) are associated with syndromic forms of craniosynostosis. Noggin, an antagonist of bone morphogenetic proteins (BMPs), is required for embryonic neural tube, somites and skeleton patterning. Warren et al. (Nature. 2003 Apr. 10; 422(6932):625-9) show that noggin is expressed postnatally in the suture mesenchyme of patent, but not fusing, cranial sutures, and that noggin expression is suppressed by FGF2 and syndromic fgfr signalling. Since noggin misexpression prevents cranial suture fusion in vitro and in vivo, it is suggested that syndromic fgfr-mediated craniosynostoses may be the result of inappropriate downregulation of noggin expression, leading to abnormally high BMP activity. Thus the subject Cerberus and Coco therapeutics may be used to down-regulate BMP activity to prevent or treat such conditions.

V. Exemplary Formulations

The subject compositions may be used alone, or as part of a conjoint therapy with other compounds/pharmaceutical compositions.

The soluble Coco or Cerberus polypeptides, including the N-terminally truncated Cerberus derivative therapeutics for use in the subject methods may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the therapeutics, its use in the pharmaceutical preparation of the disclosure is contemplated. Suitable vehicles and their formulation inclusive of other proteins are described, for example, in the book *Remington's Pharmaceutical Sciences* (*Remington's Pharmaceutical Sciences*. Mack Publishing Co., Easton, Pa., USA 1985). These vehicles include injectable "deposit formulations."

Pharmaceutical formulations of the present disclosure can also include veterinary compositions, e.g., pharmaceutical preparations of the Coco or Cerberus derivative therapeutics suitable for veterinary uses, e.g., for the treatment of live stock (cow, sheep, goat, pig, and horse, etc.) or domestic animals, e.g., cats and dogs.

Methods of disclosure may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a therapeutic at a particular target site.

The pharmaceutical compositions according to the present disclosure may be administered as either a single dose or in multiple doses. The pharmaceutical compositions of the present disclosure may be administered either as individual therapeutic agents or in combination with other therapeutic agents. The treatments of the present disclosure may be combined with conventional therapies, which may be administered sequentially or simultaneously. The pharmaceutical compositions of the present disclosure may be administered by any means that enables the Coco or Cerberus derivatives to reach the targeted cells/tissues/organs. In some embodiments, routes of administration include those selected from the group consisting of oral, intravesically, intravenous, intraarterial, intraperitoneal, local administration into the blood supply of the organ in which the targeted cells reside or directly into the cells. Intravenous administration is the preferred mode of administration. It may be accomplished with the aid of an infusion pump.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, intravesically, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically acceptable dosage forms such as described below or by other conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the particular therapeutic employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above. Generally, intravenous, intracerebroventricular and subcutaneous doses of the compounds of this disclosure for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other non-human mammals such as equines, cattle, swine and sheep; and poultry and pets in general.

The compound of the disclosure can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Combined with certain formulations, the subject Coco or Cerberus derivatives can be effective soluble agents. The therapeutic polypeptide can be provided a fusion peptide along with a second peptide which promotes solubility. To illustrate, the Cerberus derivatives of the present disclosure can be provided as part of a fusion polypeptide with all or a fragment of the hinge or Fc portion of the immunoglobulin, which can promote solubility and/or serum stability.

The present disclosure also contemplates a peptidomimetic sequence of the subject polypeptide derivatives as described herein.

Generally, the nomenclature used herein and the laboratory procedures utilized in the present disclosure include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" ($8^{th}$ Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXEMPLIFICATION

The disclosure now being generally described, it will be more readily understood by reference to the following examples, which are included merely for purposes of illustration of certain embodiments and embodiments of the present disclosure, and are not intended to limit the disclosure.

Example 1

Sources of Caronte and Human Cerberus Protein

Caronte-Fc (Cerberus homolog from *Gallus gallus*) was ordered from R&D Systems (Minneapolis, Minn.).

Full-length and N-terminally truncated forms of human Cerberus sequence were cloned into a human CMV derived expression vector, either with or without a C-terminal fusion to an Fc portion of IgG1 (both human and murine IgG1 Fc fusions were produced). These constructs were transiently transfected in HEK293 cells using polyethylenimine (PEI). After culturing, cells were harvested and conditioned media was collected for purification.

The following constructs were tested:

```
Human Cerberus, full length, no Fc (SEQ ID NO: 11)
MHLLLFQLLV LLPLGKTTRH QDGRQNQSSL SPVLLPRNQR

ELPTGNHEEA EEKPDLFVAV PHLVATSPAG EGQRQREKML

SRFGRFWKKP EREMHPSRDS DSEPFPPGTQ SLIQPIDGMK

MEKSPLREEA KKFWHHFMFR KTPASQGVIL PIKSHEVHWE

TCRTVPFSQT ITHEGCEKVV VQNNLCFGKC GSVHFPGAAQ

HSHTSCSHCL PAKFTTMHLP LNCTELSSVI KVVMLVEECQ

CKVKTEHEDG HILHAGSQDS FIPGVSA
```

Human Cerberus, full length, Fc (TGGG linker (SEQ ID NO: 27) and Fc, underlined; native signal sequence underlined with dotted line) (SEQ ID NO:12)

```
MHLLLFQLLV LLPLGKTTRH QDGRQNQSSL SPVLLPRNQR ELPTGNHEEA EEKPDLFVAV
PHLVATSPAG EGQRQREKML SRFGRFWKKP EREMHPSRDS DSEPFPPGTQ SLIQPIDGMK
MEKSPLREEA KKFWHHFMFR KTPASQGVIL PIKSHEVHWE TCRTVPFSQT ITHEGCEKVV
VQNNLCFGKC GSVHFPGAAQ HSHTSCSHCL PAKFTTMHLP LNCTELSSVI KVVMLVEECQ
CKVKTEHEDG HILHAGSQDS FIPGVSA TGGGTHTCPP CPAPELLGGP SVFLFPPKPK
DTLMISRTPE VTCVVVDVSH EDPEVKFNWY VDGVEVHNAK TKPREEQYNS TYRVVSVLTV
LHQDWLNGKE YKCKVSNKAL PVPIEKTISK AKGQPREPQV YTLPPSREEM TKNQVSLTCL
VKGFYPSDIA VEWESNGQPE NNYKTTPPVL DSDGSFFLYS KLTVDKSRWQ QGNVFSCSVM
HEALHNHYTQ KSLSLSPGK
```

Human Cerberus, short form, Fc (TGGG linker (SEQ ID NO: 27) and Fc, underlined) (SEQ ID NO:13)

```
EVHWETCRTV PFSQTITHEG CEKVVQNNL CFGKCGSVHF PGAAQHSHTS CSHCLPAKFT

TMHLPLNCTE LSSVIKVVML VEECQCKVKT EHEDGHILHA GSQDSFIPGV SA TGGGTHTCPP

CPAPELLGGP SVFLFPPKPK DTLMISRTPE VTCVVVDVSH EDPEVKFNWY VDGVEVHNAK

TKPREEQYNS TYRVVSVLTV LHQDWLNGKE YKCKVSNKAL PVPIEKTISK AKGQPREPQV

YTLPPSREEM TKNQVSLTCL VKGFYPSDIA VEWESNGQPE NNYKTTPPVL DSDGSFFLYS

KLTVDKSRWQ QGNVFSCSVM HEALHNHYTQ KSLSLSPGK
```

Three different leader sequences were considered:

```
(i) Honey bee mellitin (HBML):
MKFLVNVALVFMVVYISYIYA      (SEQ ID NO: 14)

(ii) Tissue Plasminogen Activator (TPA):
MDAMKRGLCCVLLLCGAVFVSP     (SEQ ID NO: 15)

(iii) Native:
MHLLLFQLLV LLPLGKT.        (SEQ ID NO: 16)
```

A heterologous or native leader sequence may be fused to the protein sequence at any position within the first 30 amino acids. Modeling suggests that the native leader would yield a product beginning with "TRH..." at position 18. Analysis of products expressed herein indicates that the native leader more typically yields a product beginning "KTT..." at position 16. Therefore, heterologous leader sequences may be fused N-terminal to position 16 or position 18.

Example 2

Caronte Binds 11

Figure 2:
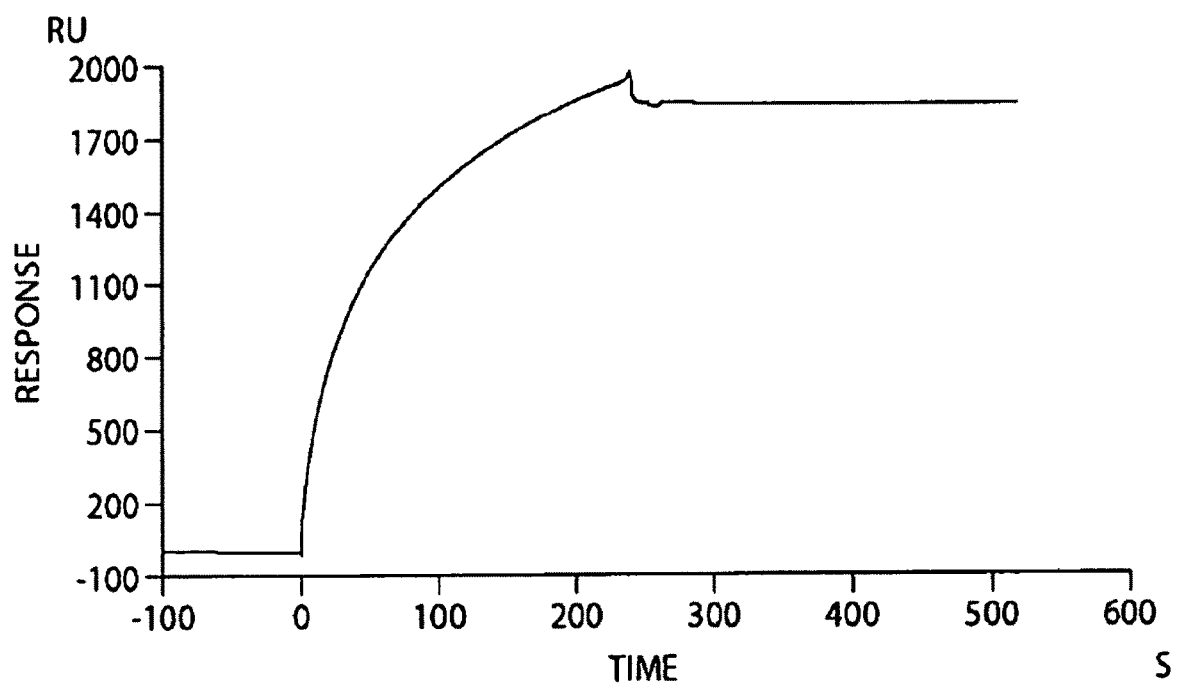
FIG. 2 Binding of Caronte-Fc to 11. The tracing shows that Caronte-Fc binds to 11 on a BiaCore chip. 11 was immobilized on a BiaCore CM5 chip using standard amine coupling procedure. Trace: Caronte-Fc (200 µg/ml; R&D Systems) was injected on the 11 coupled chip.

11 is a close homolog of myostatin that regulates neurological processes. 11 was immobilized on a BiaCore CM5 chip using standard amine coupling procedure. Trace: Caronte (200 µg/ml; R&D Systems) was injected on the 11 coupled chip. The tracing in FIG. 2 shows binding of Caronte to 11.

Example 3

Caronte and Human Cerberus Inhibit 11 and Myostatin-Mediated Signaling

Figure 3:
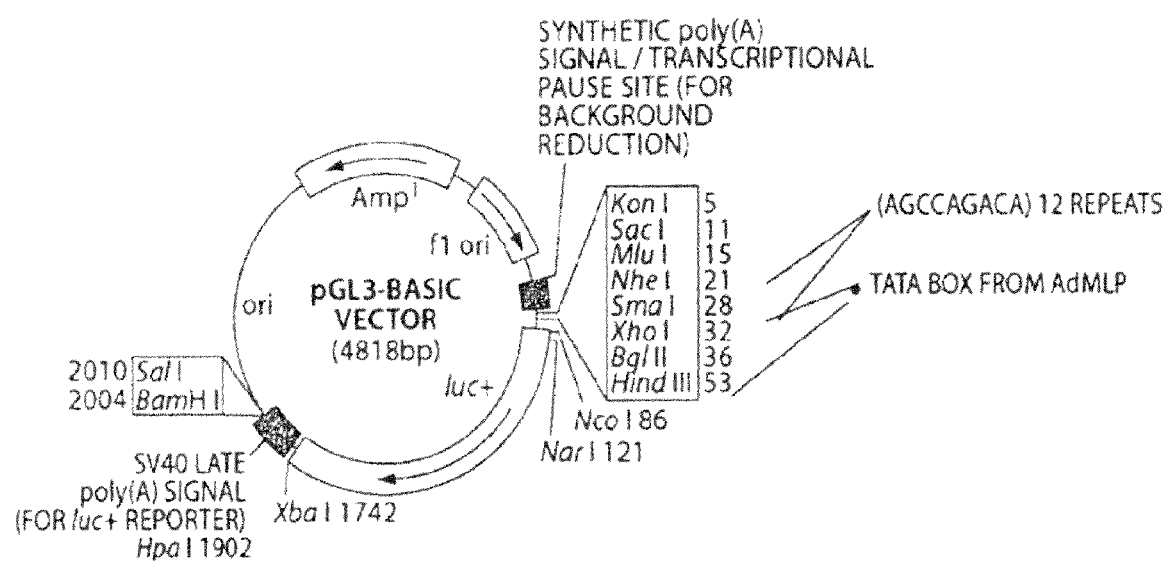
FIG. 3 A-204 Reporter Gene Assay. The figure shows the Reporter vector: pGL3(CAGA)12 (described in Dennler et al, 1998, EMBO 17: 3091-3100.) The CAGA12 motif (SEQ ID NO: 30) is present in TGF-Beta responsive genes (PAI-1 gene), so this vector is of general use for factors signaling through Smad2 and 3.

An A-204 Reporter Gene Assay was used to evaluate the effects of Caronte and Cerberus on signaling by 11, myostatin and Activin A. Cell line: Human Rhabdomyosarcoma (derived from muscle). Reporter vector: pGL3(CAGA)12 (Described in Dennler et al, 1998, EMBO 17: 3091-3100.) See FIG. 3. The CAGA12 motif is present in TGF-Beta responsive genes (PAI-1 gene), so this vector is of general use for factors signaling through Smad2 and 3.

Day 1: Split A-204 cells into 48-well plate.
Day 2: A-204 cells transfected with 10 ug pGL3(CAGA)12 or pGL3(CAGA)12(10 ug)+pRLCMV (1 ug) and Fugene.
Day 3: Add factors (diluted into medium+0.1% BSA). Inhibitors need to be preincubated with Factors for 1 hr before adding to cells. 6 hrs later, cells rinsed with PBS, and lyse cells.

This is followed by a Luciferase assay. In the absence of any inhibitors, Activin A showed 10 fold stimulation of reporter gene expression and an ED50~2 ng/ml. GDF-8: ED50: ~5 ng/ml, 15 fold stimulation. 11: 16 fold stimulation, ED50: ~1.5 ng/ml.

Figure 4:
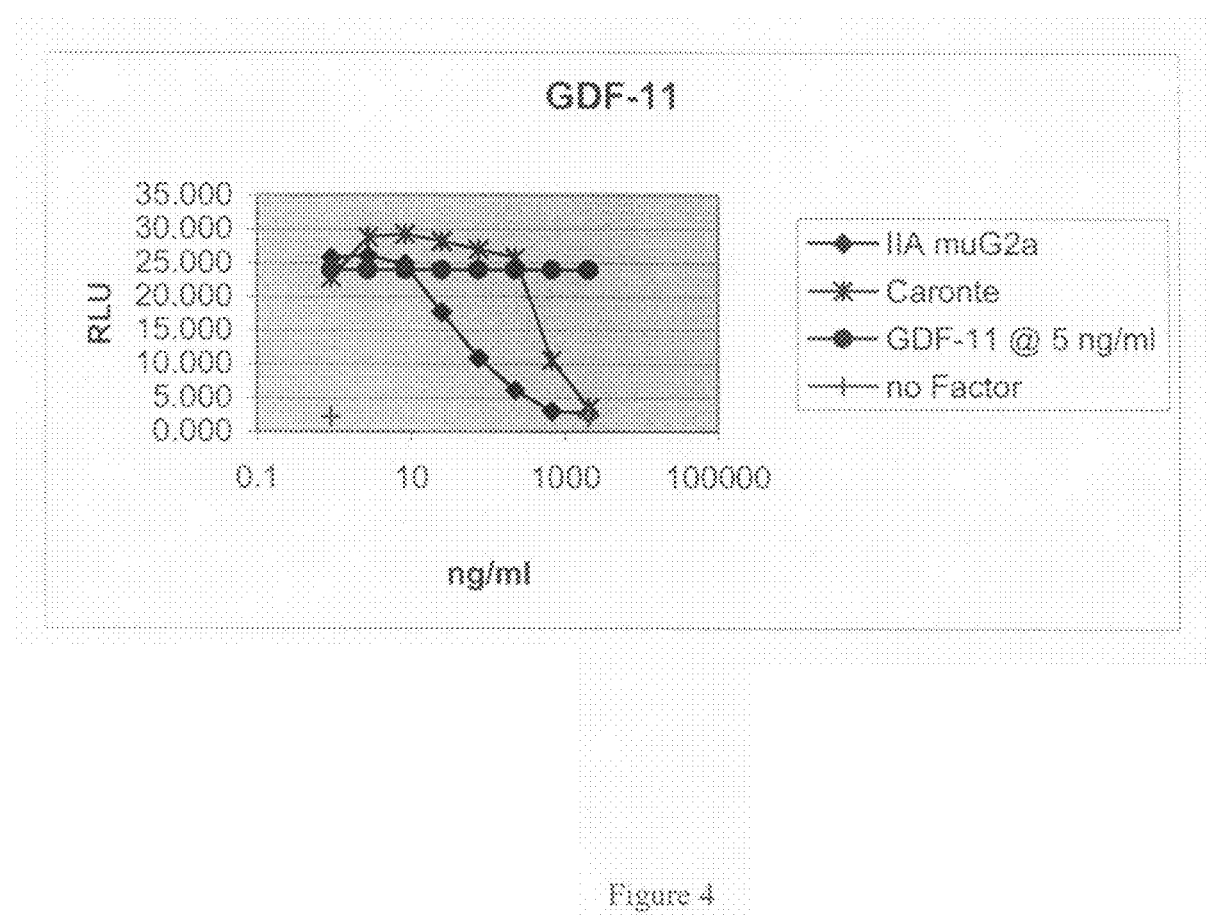
FIG. 4 Caronte-Fc inhibits 11 signaling in the A-204 Reporter Gene Assay. An ActRIIA-Fc ("IIA muG2a") fusion also inhibits 11 signaling.
Figure 5:
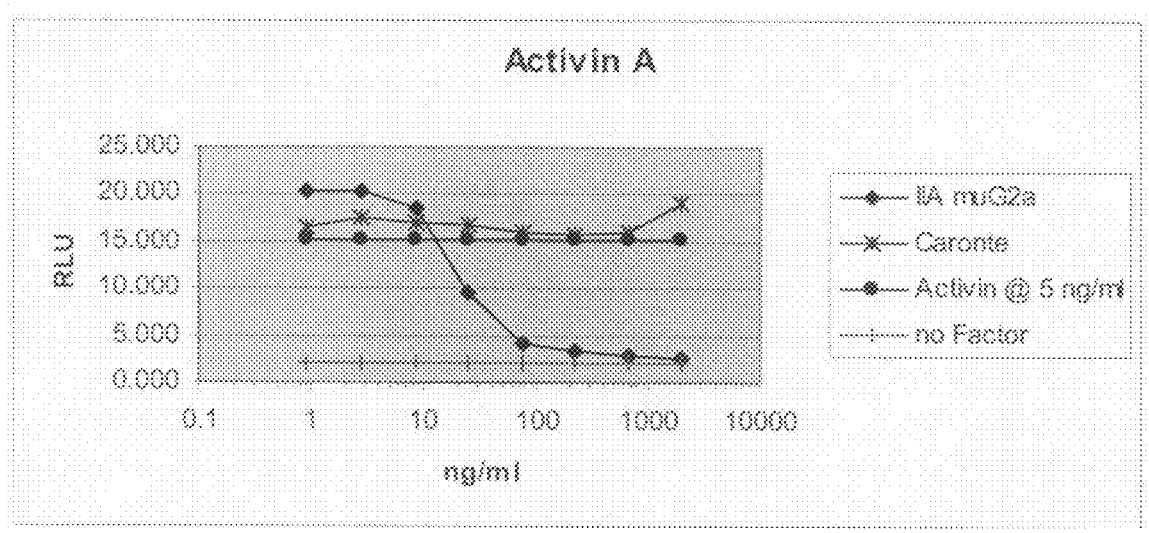
FIG. 5 Caronte-Fc does not inhibit Activin A in the A-204 Reporter Gene Assay. An ActRIIA-Fc fusion ("IIA muG2a"), as expected, does inhibit Activin A signaling.
Figure 6:
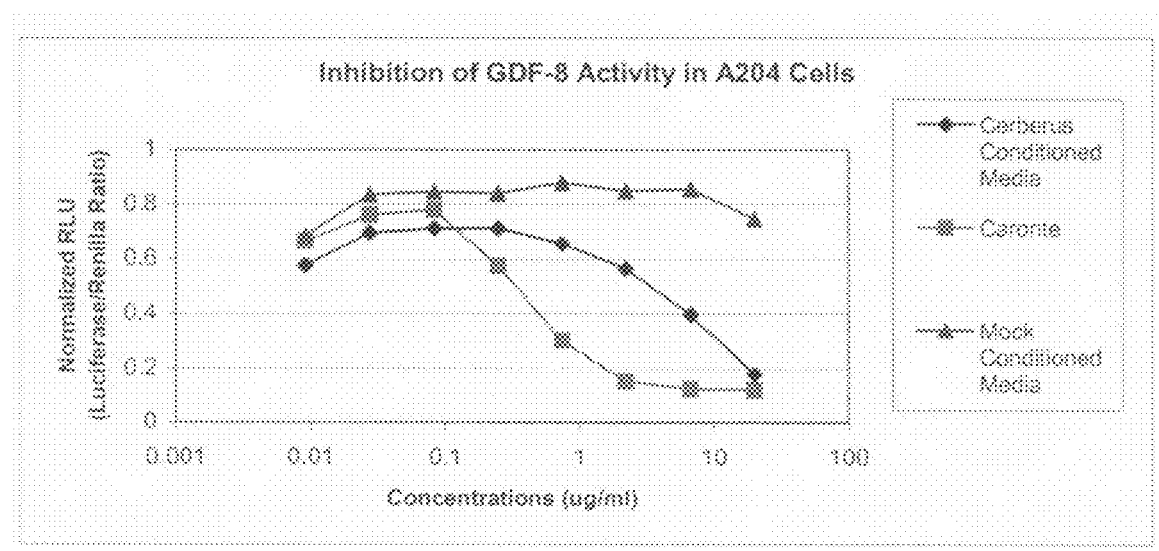
FIG. 6 Cerberus-Fc and Caronte-Fc both inhibit GDF-8 signaling in the A-204 Reporter Gene Assay.

As shown in FIG. 4, Caronte inhibits 11 signaling in the A-204 Reporter Gene Assay. An ActRIIA-Fc ("IIA muG2a") fusion also inhibits 11 signaling. As shown in FIG. 5, Caronte does not inhibit Activin A in the A-204 Reporter Gene Assay. An ActRIIA-Fc fusion ("IIA muG2a"), as expected, does inhibit Activin A signaling. Thus, Caronte is a selective inhibitor of 11/myostatin while not affecting Activin A signaling. This type of selectivity suggests that Caronte, Cerberus and Coco will have relatively few side effects when used as a therapeutic. As expected, Cerberus behaved much like Caronte, and inhibited myostatin signaling. See FIG. 6. Similar experiments were conducted to test the binding of human Cerberus and Coco to Activin A, and these experiments confirm that these molecules do not bind to Activin A.

Example 4

Sources of Human Coco Protein

Full-length human Coco was cloned into a human CMV derived expression vector, either with or without a C-terminal fusion to an Fc portion of IgG1 (both human and murine IgG1 Fc fusions were produced). These constructs were transiently transfected in HEK293 cells using polyethylenimine (PEI). After culturing, cells were harvested and conditioned media was collected for purification.

The following construct was made, and a murine Fc fusion was made also, and used in the assays presented herein:

```
Human Coco, full length, Fc (TGGG linker and mFc)
                                                 (SEQ ID NO: 17)
MLLGQLSTLL CLLSGALPTG SGRPEPQSPR PQSWAAANQT WALGPGALPP LVPASALGSW

KAFLGLQKAR QLGMGRLQRG QDEVAAVTLP LNPQEVIQGM CKAVPFVQVF SRPGCSAIRL

RNHLCFGNCS SLYIPGSDPT PLVLCNSCMP ARKRWAPVVL WCLTGSSASR RRVKISTMLI

EGCHCSPKA TGGGTHTCPP CPAPELLGGP SVFLFPPKPK DTLMISRTPE VTCVVVDVSH

EDPEVKFNWY VDGVEVHNAK TKPREEQYNS TYRVVSVLTV LHQDWLNGKE YKCKVSNKAL

PVPIEKTISK AKGQPREPQV YTLPPSREEM TKWQVSLTCL VKGFYPSDIA VEWESNGQPE

NNYKTTPPVL DSDGSFFLYS KLTVDKSRWQ QGNVFSCSVM HEALHNHYTQ KSLSLSPGK
```

The following construct is analogous to the short form Cerberus-Fc fusion protein:

```
Human Coco, short form, Fc (TGGG linker and mFc)
                                                 (SEQ ID NO: 18)
LNPQEVIQGM CKAVPFVQVF SRPGCSAIRL

RNHLCFGHCS SLYIPGSDPT PLVLCNSCMP ARKRWAPVVL WCLTGSSASR RRVKISTMLI

EGCNCSPKA TGGGTHTCPP CPAPELLGGP SVFLFPPKPK DTLMISRTPE VTCVVVDVSH

EDPEVKFNWY VDGVEVHNAK TKPREEQYNS TYRVVSVLTV LHQDWLNGKE YKCKVSNKAL

PVPIEKTISK AKGQPREPQV YTLPPSREEM TKNQVSLTCL VKGFYPSDIA VEWESNGQPE

NNYKTTPPVL DSDGSFFLYS KLTVDKSRWQ QGNVFSCSVM HEALHNHYTQ KSLSLSPGK
```

Three different leader sequences were considered:

```
(i) Honey bee mellitin (HBML):
    MKFLVNVALVFMVVYISYIYA          (SEQ ID NO: 14)

(ii) Tissue Plasminogen Activator (TPA):
    MDAMKRGLCCVLLLCGAVFVSP         (SEQ ID NO: 15)

(iii) Native:
    MLLGQLSTLL CLLSGALPTG S.       (SEQ ID NO: 19)
```

Heterologous or native leader sequences may be fused anywhere in the first 30 amino acids, and particularly N-terminal to any of amino acids 16-23.

Example 5

Human Coco Inhibits 11 Signaling

Figure 8:
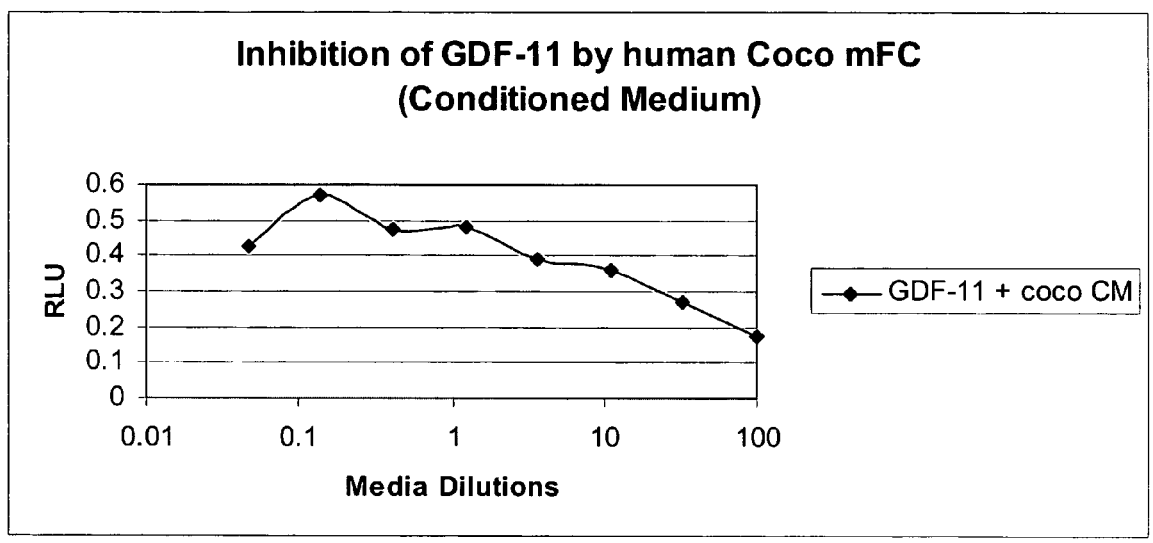
FIG. 8 Human Coco-Fc (murine Fc) inhibits 11 signaling in a cell based assay. Conditioned medium from cells expressing human Coco-mFc was tested for effects on A-204 reporter gene expression in the presence of 11.

Conditioned medium from cells expressing human Coco-mFc was tested for effects on A-204 reporter gene expression in the presence of 11. As shown in FIG. 8, conditioned medium containing Coco-mFc inhibits 11 signaling in the A-204 Reporter Gene Assay, much like Cerberus. Similar experiments showed that Coco-mFc inhibits Nodal signaling.

Example 6

Human Cerberus-Fc is Degraded in Human Serum

Figure 7:
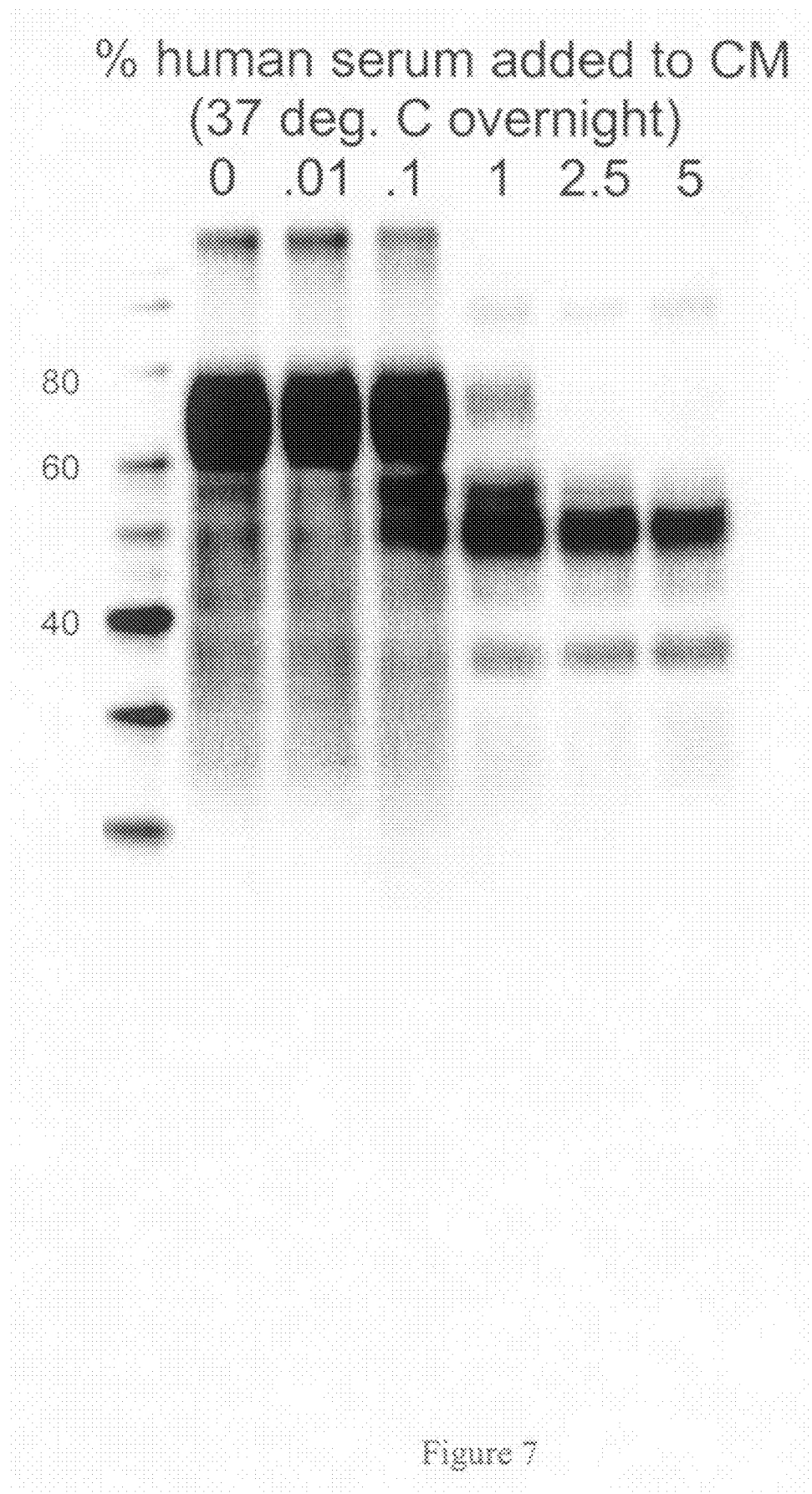
FIG. 7 Human Cerberus-Fc is degraded in human serum. Conditioned medium from cells expressing human Cerberus-Fc was incubated overnight at 37 deg. C. with varying amounts of human serum (percentages of serum added are shown at top), and resolved by SDS-PAGE. Cerberus was detected by Western blot with a primary antibody: biotinylated polyclonal anti-cerberus, and a secondary antibody: avidin-HRP. The left lane is molecular weight standards. The major band, at roughly 70 kD is Cerberus-Fc, which is completely degraded when incubated with 5% human serum.

The stability of Cerberus polypeptides in the presence of serum was evaluated. Conditioned medium from cells expressing human full-length Cerberus-Fc was incubated overnight at 37 deg. C. with varying amounts of human serum (percentages of serum added are shown at top), and resolved by SDS-PAGE. Western blot (FIG. 7) showed that Cerberus was completely degraded when incubated with 5% human serum.

N-terminal sequencing of cleavage fragments revealed that proteolysis occurred at the following sites (cleavage shown by ^):

```
38    NQR^ELP    43    (SEQ ID NO: 24)
138   MFR^KTP    143   (SEQ ID NO: 23)
207   SHC^LPA    212   (SEQ ID NO: 28)
```

Example 7

Serum Stable Human Cerberus and Coco Polypeptides

To produce serum-stable Cerberus polypeptides, a variety of mutations may be introduced at cleavage sites and the surrounding sequences. In short forms of Cerberus, only the L212 cleavage site remains (amino acid numbering is with reference to the full length, native Cerberus sequence, SEQ ID NO: 2), and so a mutation of any, some or all of the amino acids in the sequence SHCLPA (SEQ ID NO: 28) may be altered to eliminate this cleavage site. Generally, mutations will be to small, uncharged groups, such as alanine or serine. Mutations of C211 and/or L212 to serine or alanine are particularly desirable. In addition, or in the alternative, an N-linked glycosylation site (NXT/S) may be introduced at a position within the range of amino acids 202-222. An N-linked glycosylation site may also be introduced at a position that is expected to be proximal to the 212 position in the three-dimensional structure of the protein. Similar mutations may be made at each of the other sites 38 NQR^ELP 43 (SEQ ID NO: 24) and 138 MFR^KTP 143 (SEQ ID NO: 23), depending on the length of the Cerberus molecule to be employed. A particularly desirable mutation with respect to the 38 NQR^ELP 43 (SEQ ID NO: 24) cleavage site is an R to S/T mutation to make the sequence 38 NQ(S/T)ELP 43 (SEQ ID NO: 29), simultaneously eliminating the cleavage site and introducing an N-linked glycosylation site. Additionally, experiments have shown that products cleaved at E41 and K141 retain myostatin binding activity. Accordingly, N-terminally truncated forms of Cerberus, beginning at E41 or K141 will be resistant to cleavage at these sites and retain activity. The activity of the short form suggests that a minimal myostatin binding domain is the cysteine knot, located at amino acids 162-241 of SEQ ID NO:2.

Cerberus constructs with one or more of the alterations (shown in brackets below; e.g., "[R(T)]" means that an arginine normally at the position may be replaced with a threonine) will have N-linked glycosylation sites that will block cleavage and are expected to confer improved pharmacokinetic properties. The constructs below may be expressed, for example, with a tPA leader sequence and an Fc sequence.

```
                                              (SEQ ID NO: 20)
TRHQDGRQNQSSLSPVLLPRNQ[R(T)]ELPTGNHEEAEEKYDLFVAVPH

LVATSPAGEGQRQREKMLSRFGRFWKKPEREMHPSRDSDSEPFPPGTQSL

IQPIDGMKMEKSPLREEAKKFWHHFMF[R(N)]KTPASQGVILPIKSHEV

HWETCRTVPFSQTITHEGCEKVVVQNNLCFGKCGSVHFPGAAQHSHTSCS

HCLPAKFTTMHLPLNCTELSSVIKVVMLVEECQCKVKTEHEDGHILH[A (N)]GSQDSFIP[G(N)]VSATG
```

It is expected that Coco will behave in a manner similar to Cerberus, however, the two likely cleavage sites in Coco occur within the cysteine knot domain at the sequences: 150 PAR^KRW 155 (SEQ ID NO: 25) and 168 SRR^RVK 173 (SEQ ID NO: 26). Amino acids in these positions may be altered to eliminate the cleavage, with alanine and serine being preferred amino acids. In addition, or in the alternative, an N-linked glycosylation site (NXT/S) may be introduced at or near either of these positions. The activity of the short form of Cerberus suggests that a minimal myostatin binding domain of Coco is the cysteine knot, located at amino acids 101-185 of SEQ ID NO:5.

Coco constructs with one or more of the alterations (shown in brackets below) will have N-linked glycosylation sites that will block cleavage and are expected to confer improved pharmacokinetic properties. The constructs below may be expressed, for example, with a tPA leader sequence and an Fc sequence.

```
                                              (SEQ ID NO: 21)
GRPEPQSPRPQSWAAANQTWALGPGAIPPLVPASALGSWKAFLGLQKARQ

LGMG[R(N)]L[Q(T)]RGQDEVAAVTLPLNPQEVIQGMCKAVPFVQVFS

RPGCSAIRLRNHLCFGHCSSLYIPGSDPTPLVLCNSCMPA[R(N)]K[R (T)]WAPVVLWCLTGSSASR[R(N)][R(A)][V(S)]KISTMLIEGCHC

SPKA
```

Example 8

Cysteine Variants of Cerberus and Coco

In some proteins, odd numbers of cysteine residues result in a free sulfhydryl group that may cause protein aggregation or otherwise interfere with protein production. Both native Coco and native Cerberus have odd numbers of cystein residues. In order to improve the expression of Cerberus, variants with fewer cysteine residues were generated, as well as variants with changes in proximity to one or more of the cysteines. Relative to SEQ ID NO:2, the following variants were generated:

C176G;

C206G;

C223G;

N222D.

Each of these proteins were expressible and retained binding to GDF11, indicating that the biochemical activity of these proteins remained intact. Similar specific variants may be made with respect to Coco (relative to SEQ ID NO:5):

C115G;

C145G;

C162G.

Therefore, the disclosure provides Cerberus and Coco variants in which one or more cysteine residues are deleted or replaced. If replaced, the replacement amino acid may be any of the other 19 canonical amino acids, although G, A, S and T are preferred.

EQUIVALENTS

A skilled artisan will recognize, or be able to ascertain using no more than routine experimentation, many equivalents to the specific embodiments of the inventions described herein. Such equivalents are intended to be encompassed by the following claims.

---

We claim:

1. An isolated myostatin antagonist protein, the protein comprising an amino acid sequence that has at least 90% identity to the sequence of amino acids 22-185 of human Coco (SEQ ID NO:5), wherein said protein comprises a modification with respect to the sequence of amino acids 22-185 of SEQ ID NO: 5 such that cleavage in human serum is reduced or eliminated, and wherein said protein is substantially serum stable for a period of at least 24 hours.

2. The myostatin antagonist protein of claim 1, wherein the protein comprises an amino acid sequence that has at least 90% identity to the sequence of amino acids 22-189 of human Coco.

3. The myostatin antagonist protein of claim 1, wherein the protein retains at least 50% of the myostatin antagonist activity after exposure to human serum for 24 hours at 37° C.

4. The myostatin antagonist protein of claim 1, wherein myostatin antagonist activity is assessed in an A204 cell based assay.

5. The myostatin antagonist protein of claim 1, wherein the protein comprises a modification with respect to the amino acid sequence of SEQ ID NO:5 that reduces or eliminates cleavage within one or both of the following sequences of human Coco: PARKRW (SEQ ID NO: 25) and SRRRVK (SEQ ID NO: 26).

6. A pharmaceutical preparation comprising a myostatin antagonist protein of claim 1.

* * * * *

SEQUENCE LISTING

```
<160> NUMBER OF SEQ ID NOS: 30

<210> SEQ ID NO 1
<211> LENGTH: 272
<212> TYPE: PRT
<213> ORGANISM: Mus musculus

<400> SEQUENCE: 1

Met His Leu Leu Leu Val Gln Leu Leu Val Leu Leu Pro Leu Gly Lys
1               5                   10                  15

Ala Asp Leu Cys Val Asp Gly Cys Gln Ser Gln Gly Ser Leu Ser Phe
                20                  25                  30

Pro Leu Leu Glu Arg Gly Arg Arg Asp Leu His Val Ala Asn His Glu
            35                  40                  45

Glu Ala Glu Asp Lys Pro Asp Leu Phe Val Ala Val Pro His Leu Met
    50                  55                  60

Gly Thr Ser Leu Ala Gly Glu Gly Gln Arg Gln Arg Gly Lys Met Leu
65                  70                  75                  80

Ser Arg Leu Gly Arg Phe Trp Lys Lys Pro Glu Thr Glu Phe Tyr Pro
                85                  90                  95

Pro Arg Asp Val Glu Ser Asp His Val Ser Ser Gly Met Gln Ala Val
            100                 105                 110

Thr Gln Pro Ala Asp Gly Arg Lys Val Glu Arg Ser Pro Leu Gln Glu
        115                 120                 125

Glu Ala Lys Arg Phe Trp His Arg Phe Met Phe Arg Lys Gly Pro Ala
    130                 135                 140

Phe Gln Gly Val Ile Leu Pro Ile Lys Ser His Glu Val His Trp Glu
145                 150                 155                 160

Thr Cys Arg Thr Val Pro Phe Asn Gln Thr Ile Ala His Glu Asp Cys
                165                 170                 175

Gln Lys Val Val Val Gln Asn Asn Leu Cys Phe Gly Lys Cys Ser Ser
            180                 185                 190

Ile Arg Phe Pro Gly Glu Gly Ala Asp Ala His Ser Phe Cys Ser His
        195                 200                 205

Cys Ser Pro Thr Lys Phe Thr Thr Val His Leu Met Leu Asn Cys Thr
```

```
            210                 215                 220
Ser Pro Thr Pro Val Val Lys Met Val Met Gln Val Glu Glu Cys Gln
225                 230                 235                 240

Cys Met Val Lys Thr Glu Arg Gly Glu Arg Leu Leu Leu Ala Gly
                245                 250                 255

Ser Gln Gly Ser Phe Ile Pro Gly Leu Pro Ala Ser Lys Thr Asn Pro
                260                 265                 270

<210> SEQ ID NO 2
<211> LENGTH: 267
<212> TYPE: PRT
<213> ORGANISM: Homo sapiens

<400> SEQUENCE: 2

Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
                20                  25                  30

Val Leu Leu Pro Arg Asn Gln Arg Glu Leu Pro Thr Gly Asn His Glu
            35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
                100                 105                 110

Ile Gln Pro Ile Asp Gly Met Lys Met Glu Lys Ser Pro Leu Arg Glu
            115                 120                 125

Glu Ala Lys Lys Phe Trp His His Phe Met Phe Arg Lys Thr Pro Ala
    130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
                180                 185                 190

Val His Phe Pro Gly Ala Ala Gln His Ser His Thr Ser Cys Ser His
            195                 200                 205

Cys Leu Pro Ala Lys Phe Thr Thr Met His Leu Pro Leu Asn Cys Thr
    210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala
                260                 265

<210> SEQ ID NO 3
<211> LENGTH: 1752
<212> TYPE: DNA
<213> ORGANISM: Mus musculus
<220> FEATURE:
<221> NAME/KEY: MOD_RES
<222> LOCATION: (1235)..(1235)
<223> OTHER INFORMATION: a, c, g, t, unknown or other
```

```
<220> FEATURE:
<221> NAME/KEY: MOD_RES
<222> LOCATION: (1313)..(1313)
<223> OTHER INFORMATION: a, c, g, t, unknown or other

<400> SEQUENCE: 3
gggggggggg ggggtcagag ggagctttct tttaggcccg tccatctgtg aatctaacct      60
cagtttctgg gaatcaggaa gcatgcatct cctcttagtt cagctgcttg ttctcttgcc     120
tctggggaag gcagacctat gtgtggatgg ctgccagagt cagggctctt tatcctttcc     180
tctcctagaa aggggtcgca gagatctcca cgtggccaac cacgaggagg cagaagacaa     240
gccggatctg tttgtggccg tgccacacct catgggcacc agcctggctg gggaaggcca     300
gaggcagaga gggaagatgc tgtccaggct tggaagattc tggaagaaac ctgagaccga     360
attttacccc ccaagggatg tggaaagcga tcatgtctca tcggggatgc aggccgtgac     420
tcagccagca gatgggagga aagtggagag atcacctcta caggaggaag ccaagaggtt     480
ctggcatcgg ttcatgttca gaaagggccc ggcgttccag ggagtcatcc tgcccatcaa     540
aagccacgaa gtacactggg agacctgcag gactgtgccc ttcaaccaga ccattgccca     600
tgaagactgt caaaaagtcg ttgtccagaa caacctttgc tttggcaaat gcagttccat     660
tcgttttccc ggagaagggg cagatgccca cagcttctgc tcccactgct cgcccaccaa     720
attcaccacc gtgcacttga tgctgaactg caccagccca accccgtgg tcaagatggt     780
gatgcaagta gaaagagtgtc agtgcatggt gaagacggaa cgtggagagg agcgcctcct     840
actggctggt tcccagggtt ccttcatccc tggacttcca gcttcaaaaa caaacccatg     900
aattacctca acagaaagca aaacctcaac agaataagtg agggttattc aatctggaaa     960
tgttatgtga gttatataaa gatcagtgga aaatatcttt ctctctccct ctctccccct    1020
ctctcttctc tctattttct ctctctctct ctctctctct ctctctctca                1080
cacacacaca cacacacaca cacacacaca catgtttgtg tttagacagg gtcttatgta    1140
ttctcagctg gcctcaaact cacaatgtgg ctggggatga ttttaaactc ctgatccaat    1200
tcctgagtgc tgggattaca gacatgctcc ataanacata gctcccagaa ggattttaa    1260
aagagatttt gcatgtttca aagttgcctt tgagactcag aaatattttg atntattgaa    1320
tggccttgcc acagatgtgg gaggcagctt gcttggtggc ccaagtattt ttttttttgtt    1380
cgttcagaat tctccacatg aagttttta c tgttggttat ctggcgttga agaaggaata    1440
gtgaaggtac ttttaacagt ttacacgtgg aaggggctca ggcactagga accaacctttt    1500
tcccggaata tgaggaaaat acatgaacag tattagagtc acttgaggaa gttactagga    1560
aacgccataa gtctccaagt acattgtgag tcatttgaa ggacaatcgt gtatatagac    1620
gaaatcttct actcgtatgc ttttgaatct tctagcaagt taggtttcta tgtttgggct    1680
tcttcctatt gtctaagagt atgtgtgaca aattcaacct gacaaatacc tcaatggcaa    1740
attctgaccc tg                                                         1752

<210> SEQ ID NO 4
<211> LENGTH: 804
<212> TYPE: DNA
<213> ORGANISM: Homo sapiens

<400> SEQUENCE: 4
atgcatctcc tcttatttca gctgctggta ctcctgcctc taggaaagac cacacggcac      60
caggatggcc gccagaatca gagttctctt tccccgtac tcctgccaag gaatcaaaga     120
```

```
gagcttccca caggcaacca tgaggaagct gaggagaagc cagatctgtt tgtcgcagtg      180
ccacaccttg tagccaccag ccctgcaggg aaggccaga ggcagagaga aagatgctg        240 tccagatttg gcaggttctg gaagaagcct gagagagaaa tgcatccatc cagggactca    300
gatagtgagc ccttcccacc tgggacccag tccctcatcc agccgataga tggaatgaaa    360
atggagaaat ctcctcttcg ggaagaagcc aagaaattct ggcaccactt catgttcaga    420
aaaactccgg cttctcaggg ggtcatcttg cccatcaaaa gccatgaagt acattgggag    480
acctgcagga cagtgccctt cagccagact ataacccacg aaggctgtga aaaagtagtt    540
gttcagaaca acctttgctt tgggaaatgc gggtctgttc attttcctgg agccgcgcag    600
cactcccata cctcctgctc tcactgtttg cctgccaagt tcaccacgat gcacttgcca    660
ctgaactgca ctgaactttc tccgtgatca aggtggtga tgctggtgga ggagtgccag      720
tgcaaggtga agacggagca tgaagatgga cacatcctac atgctggctc ccaggattcc    780
tttatcccag gagtttcagc ttga                                            804
```

```
<210> SEQ ID NO 5
<211> LENGTH: 189
<212> TYPE: PRT
<213> ORGANISM: Homo sapiens

<400> SEQUENCE: 5

Met Leu Leu Gly Gln Leu Ser Thr Leu Leu Cys Leu Leu Ser Gly Ala
1               5                   10                  15

Leu Pro Thr Gly Ser Gly Arg Pro Glu Pro Gln Ser Pro Arg Pro Gln
            20                  25                  30

Ser Trp Ala Ala Ala Asn Gln Thr Trp Ala Leu Gly Pro Gly Ala Leu
        35                  40                  45

Pro Pro Leu Val Pro Ala Ser Ala Leu Gly Ser Trp Lys Ala Phe Leu
    50                  55                  60

Gly Leu Gln Lys Ala Arg Gln Leu Gly Met Gly Arg Leu Gln Arg Gly
65                  70                  75                  80

Gln Asp Glu Val Ala Ala Val Thr Leu Pro Leu Asn Pro Gln Glu Val
                85                  90                  95

Ile Gln Gly Met Cys Lys Ala Val Pro Phe Val Gln Val Phe Ser Arg
            100                 105                 110

Pro Gly Cys Ser Ala Ile Arg Leu Arg Asn His Leu Cys Phe Gly His
        115                 120                 125

Cys Ser Ser Leu Tyr Ile Pro Gly Ser Asp Pro Thr Pro Leu Val Leu
    130                 135                 140

Cys Asn Ser Cys Met Pro Ala Arg Lys Arg Trp Ala Pro Val Val Leu
145                 150                 155                 160

Trp Cys Leu Thr Gly Ser Ser Ala Ser Arg Arg Val Lys Ile Ser
                165                 170                 175

Thr Met Leu Ile Glu Gly Cys His Cys Ser Pro Lys Ala
            180                 185
```

```
<210> SEQ ID NO 6
<211> LENGTH: 1731
<212> TYPE: DNA
<213> ORGANISM: Homo sapiens

<400> SEQUENCE: 6
agtccggaca gacagacagg cagacagacg cacggacaag cagatgctcc ttggccagct     60
atccactctt ctgtgcctgc ttagcggggc cctgcctaca ggctcaggga ggcctgaacc    120
```

```
ccagtctcct cgacctcagt cctgggctgc agccaatcag acctgggctc tgggcccagg      180
ggccctgccc ccactggtgc cagcttctgc ccttgggagc tggaaggcct tcttgggcct      240
gcagaaagcc aggcagctgg ggatgggcag gctgcagcgt gggcaagacg aggtggctgc      300
tgtgactctg ccgctgaacc ctcaggaagt gatccagggg atgtgtaagg ctgtgccctt      360
cgttcaggtg ttctcccggc ccggctgctc agccatacgc ctccgaaatc atctgtgctt      420
tggtcattgc tcctctctct acatccctgg ctcggacccc accccactag tcctgtgcaa      480
cagctgtatg cctgctcgca agcgttgggc accgtggtc ctgtggtgtc tcactggcag       540
ctcagcctcc cgtcgacggg tgaagatatc caccatgctg atcgaggggt gtcactgcag      600
cccaaaagca tgaactgagc atcgtggatg ggtgcacgga cacacgcacc ttggagaaat      660
gaggggagat ggaccaagaa agacgtggac ctggatgatg tactctgggt caagagacca      720
gggatgcagg gttaggcaga caggtcccca gagtcctcac cctgctcccc agacagtaga      780
cacagtgccc gtcctggagt tgcaccactg atagtcacag cacacaatga ttgacaactc      840
actttttttt ttttttttga gatggagtct cgctctgtcg cccaggctgg agtgcagtgg      900
cgcaatctca gctcactgca agctccacct cccgggttta tgccattctc ctgtctcagc      960
ctcccgagta gctgggacta caggcacccg ccaacacgcc cggctaattt ttcgtatttt     1020
tagtaaagac agggtttcac cgtgttagcc aggatggtct ctatctcctg acctcgtgat     1080
ctgcctgcct tggccttatt atttttttttt tttaaggaca gagtctctct ctgtcaccca     1140
ggctggagtg caatggcgcg atcttggctc actgtaactt ccacttgcca ggctcaagca     1200
gttctcctgc ctcagcctcc tgagtagctg ggactacagg cacccgccac catgcccagc     1260 taattttttgt attttagtta gagacagagt ttcaccatat tagcctggct ggtctcaaac     1320
tcctggcctc aggtgatctg cccacctcgg cctcccaaag tgctgggatc aaatccactg     1380
ttaatcatta ggctgaactg tctcttatag aatgaggtca aagacactcc cagttgcagg     1440
gagggtagat ggccccaccc agaccgagag acacagtgat gacctcagcc tagggacacc     1500
aaaaaaaaaa aaaaaaaaaa cccaaaccaa aaacgcaaac caaagcaggc aggcagacag     1560
ctgctggggg aaatcctggg gtccttgaga cagaggcagg accctcgtgt cccagctgc      1620 ctcttgcctt gatagtggtg ctgtgtccct ctcagacccc ccacctgagt ctccacagag     1680
ccccacgcct ggcatggcat tccacagaaa ccataaaggt tggctgagtc c              1731
```

<210> SEQ ID NO 7
<211> LENGTH: 14
<212> TYPE: PRT
<213> ORGANISM: Homo sapiens

<400> SEQUENCE: 7

Pro Pro Gly Thr Gln Ser Leu Ile Gln Pro Ile Asp Gly Met
1               5                   10

<210> SEQ ID NO 8
<211> LENGTH: 27
<212> TYPE: PRT
<213> ORGANISM: Homo sapiens

<400> SEQUENCE: 8

Cys Lys Val Lys Thr Glu His Glu Asp Gly His Ile Leu His Ala Gly
1               5                   10                  15

Ser Gln Asp Ser Phe Ile Pro Gly Val Ser Ala
            20                  25

```
<210> SEQ ID NO 9
<211> LENGTH: 75
<212> TYPE: PRT
<213> ORGANISM: Homo sapiens

<400> SEQUENCE: 9

Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro
65                  70                  75

<210> SEQ ID NO 10
<211> LENGTH: 70
<212> TYPE: PRT
<213> ORGANISM: Homo sapiens

<400> SEQUENCE: 10

Ala Leu Leu Cys Ala Cys Thr Ser Cys Leu Gln Ala Asn Tyr Thr Cys
1               5                   10                  15

Glu Thr Asp Gly Ala Cys Met Val Ser Ile Phe Asn Leu Asp Gly Met
            20                  25                  30

Glu His His Val Arg Thr Cys Ile Pro Lys Val Glu Leu Val Pro Ala
        35                  40                  45

Gly Lys Pro Phe Tyr Cys Leu Ser Ser Glu Asp Leu Arg Asn Thr His
    50                  55                  60

Cys Cys Tyr Thr Asp Tyr
65                  70

<210> SEQ ID NO 11
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
                100                 105                 110
```

```
Ile Gln Pro Ile Asp Gly Met Lys Met Glu Lys Ser Pro Leu Arg Glu
            115                 120                 125

Glu Ala Lys Lys Phe Trp His His Phe Met Phe Arg Lys Thr Pro Ala
130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205

Cys Leu Pro Ala Lys Phe Thr Thr Met His Leu Pro Leu Asn Cys Thr
    210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala
            260                 265

<210> SEQ ID NO 12
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
                20                  25                  30

Val Leu Leu Pro Arg Asn Gln Arg Glu Leu Pro Thr Gly Asn His Glu
            35                  40                  45

Glu Ala Glu Glu Lys Pro Asp Leu Phe Val Ala Val Pro His Leu Val
        50                  55                  60

Ala Thr Ser Pro Ala Gly Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
        115                 120                 125

Glu Ala Lys Lys Phe Trp His His Phe Met Phe Arg Lys Thr Pro Ala
    130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205
```

```
Cys Leu Pro Ala Lys Phe Thr Thr Met His Leu Pro Leu Asn Cys Thr
    210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala Thr Gly Gly Gly Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Val Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 13
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val His Trp Glu Thr Cys Arg Thr Val Pro Phe Ser Gln Thr Ile
1               5                   10                  15

Thr His Glu Gly Cys Glu Lys Val Val Val Gln Asn Asn Leu Cys Phe
            20                  25                  30

Gly Lys Cys Gly Ser Val His Phe Pro Gly Ala Ala Gln His Ser His
        35                  40                  45

Thr Ser Cys Ser His Cys Leu Pro Ala Lys Phe Thr Thr Met His Leu
    50                  55                  60

Pro Leu Asn Cys Thr Glu Leu Ser Ser Val Ile Lys Val Val Met Leu
```

```
                65                  70                  75                  80
Val Glu Glu Cys Gln Cys Lys Val Lys Thr Glu His Glu Asp Gly His
                    85                  90                  95

Ile Leu His Ala Gly Ser Gln Asp Ser Phe Ile Pro Gly Val Ser Ala
                100                 105                 110

Thr Gly Gly Thr His Thr Cys Pro Pro Cys Pro Ala Pro Glu Leu
                115                 120                 125

Leu Gly Gly Pro Ser Val Phe Leu Phe Pro Pro Lys Pro Lys Asp Thr
            130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Gln Tyr Asn Ser
            180                 185                 190

Thr Tyr Arg Val Val Ser Val Leu Thr Val Leu His Gln Asp Trp Leu
                195                 200                 205

Asn Gly Lys Glu Tyr Lys Cys Lys Val Ser Asn Lys Ala Leu Pro Val
            210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
                260                 265                 270

Val Glu Trp Glu Ser Asn Gly Gln Pro Glu Asn Asn Tyr Lys Thr Thr
            275                 280                 285

Pro Pro Val Leu Asp Ser Asp Gly Ser Phe Phe Leu Tyr Ser Lys Leu
            290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340

<210> SEQ ID NO 14
<211> LENGTH: 21
<212> TYPE: PRT
<213> ORGANISM: Apis sp.

<400> SEQUENCE: 14

Met Lys Phe Leu Val Asn Val Ala Leu Val Phe Met Val Val Tyr Ile
1               5                   10                  15

Ser Tyr Ile Tyr Ala
            20

<210> SEQ ID NO 15
<211> LENGTH: 22
<212> TYPE: PRT
<213> ORGANISM: Homo sapiens

<400> SEQUENCE: 15

Met Asp Ala Met Lys Arg Gly Leu Cys Cys Val Leu Leu Leu Cys Gly
1               5                   10                  15

Ala Val Phe Val Ser Pro
```

<210> SEQ ID NO 16
<211> LENGTH: 17
<212> TYPE: PRT
<213> ORGANISM: Homo sapiens

<400> SEQUENCE: 16

```
Met His Leu Leu Leu Phe Gln Leu Leu Val Leu Leu Pro Leu Gly Lys
1               5                   10                  15
Thr
```

<210> SEQ ID NO 17
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Leu Leu Gly Gln Leu Ser Thr Leu Cys Leu Leu Ser Gly Ala
1               5                   10                  15

Leu Pro Thr Gly Ser Gly Arg Pro Glu Pro Gln Ser Pro Arg Pro Gln
                20                  25                  30

Ser Trp Ala Ala Asn Gln Thr Trp Ala Leu Gly Pro Gly Ala Leu
            35                  40                  45

Pro Pro Leu Val Pro Ala Ser Ala Leu Gly Ser Trp Lys Ala Phe Leu
    50                  55                  60

Gly Leu Gln Lys Ala Arg Gln Leu Gly Met Gly Arg Leu Gln Arg Gly
65                  70                  75                  80

Gln Asp Glu Val Ala Ala Val Thr Leu Pro Leu Asn Pro Gln Glu Val
                85                  90                  95

Ile Gln Gly Met Cys Lys Ala Val Pro Phe Val Gln Val Phe Ser Arg
            100                 105                 110

Pro Gly Cys Ser Ala Ile Arg Leu Arg Asn His Leu Cys Phe Gly His
        115                 120                 125

Cys Ser Ser Leu Tyr Ile Pro Gly Ser Asp Pro Thr Pro Leu Val Leu
    130                 135                 140

Cys Asn Ser Cys Met Pro Ala Arg Lys Arg Trp Ala Pro Val Val Leu
145                 150                 155                 160

Trp Cys Leu Thr Gly Ser Ser Ala Ser Arg Arg Arg Val Lys Ile Ser
                165                 170                 175

Thr Met Leu Ile Glu Gly Cys His Cys Ser Pro Lys Ala Thr Gly Gly
            180                 185                 190

Gly Thr His Thr Cys Pro Pro Cys Pro Ala Pro Glu Leu Leu Gly Gly
        195                 200                 205

Pro Ser Val Phe Leu Phe Pro Pro Lys Pro Lys Asp Thr Leu Met Ile
    210                 215                 220

Ser Arg Thr Pro Glu Val Thr Cys Val Val Val Asp Val Ser His Glu
225                 230                 235                 240

Asp Pro Glu Val Lys Phe Asn Trp Tyr Val Asp Gly Val Glu Val His
                245                 250                 255

Asn Ala Lys Thr Lys Pro Arg Glu Glu Gln Tyr Asn Ser Thr Tyr Arg
            260                 265                 270

Val Val Ser Val Leu Thr Val Leu His Gln Asp Trp Leu Asn Gly Lys
        275                 280                 285
```

```
Glu Tyr Lys Cys Lys Val Ser Asn Lys Ala Leu Pro Val Pro Ile Glu
    290                 295                 300

Lys Thr Ile Ser Lys Ala Lys Gly Gln Pro Arg Glu Pro Gln Val Tyr
305                 310                 315                 320

Thr Leu Pro Pro Ser Arg Glu Glu Met Thr Lys Asn Gln Val Ser Leu
                325                 330                 335

Thr Cys Leu Val Lys Gly Phe Tyr Pro Ser Asp Ile Ala Val Glu Trp
            340                 345                 350

Glu Ser Asn Gly Gln Pro Glu Asn Asn Tyr Lys Thr Thr Pro Pro Val
        355                 360                 365

Leu Asp Ser Asp Gly Ser Phe Phe Leu Tyr Ser Lys Leu Thr Val Asp
    370                 375                 380

Lys Ser Arg Trp Gln Gln Gly Asn Val Phe Ser Cys Ser Val Met His
385                 390                 395                 400

Glu Ala Leu His Asn His Tyr Thr Gln Lys Ser Leu Ser Leu Ser Pro
                405                 410                 415

Gly Lys

<210> SEQ ID NO 18
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Leu Asn Pro Gln Glu Val Ile Gln Gly Met Cys Lys Ala Val Pro Phe
1               5                   10                  15

Val Gln Val Phe Ser Arg Pro Gly Cys Ser Ala Ile Arg Leu Arg Asn
            20                  25                  30

His Leu Cys Phe Gly His Cys Ser Ser Leu Tyr Ile Pro Gly Ser Asp
        35                  40                  45

Pro Thr Pro Leu Val Leu Cys Asn Ser Cys Met Pro Ala Arg Lys Arg
    50                  55                  60

Trp Ala Pro Val Val Leu Trp Cys Leu Thr Gly Ser Ser Ala Ser Arg
65                  70                  75                  80

Arg Arg Val Lys Ile Ser Thr Met Leu Ile Glu Gly Cys His Cys Ser
                85                  90                  95

Pro Lys Ala Thr Gly Gly Gly Thr His Thr Cys Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Val Pro Ile Glu Lys Thr Ile Ser Lys Ala Lys Gly Gln Pro
    210                 215                 220
```

```
Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
            245                 250                 255

Asp Ile Ala Val Glu Trp Glu Ser Asn Gly Gln Pro Glu Asn Asn Tyr
        260                 265                 270

Lys Thr Thr Pro Pro Val Leu Asp Ser Asp Gly Ser Phe Phe Leu Tyr
    275                 280                 285

Ser Lys Leu Thr Val Asp Lys Ser Arg Trp Gln Gln Gly Asn Val Phe
290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 19
<211> LENGTH: 21
<212> TYPE: PRT
<213> ORGANISM: Homo sapiens

<400> SEQUENCE: 19

Met Leu Leu Gly Gln Leu Ser Thr Leu Cys Leu Leu Ser Gly Ala
1               5                   10                  15

Leu Pro Thr Gly Ser
            20

<210> SEQ ID NO 20
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Arg or Thr
<220> FEATURE:
<221> NAME/KEY: MOD_RES
<222> LOCATION: (123)..(123)
<223> OTHER INFORMATION: Arg or Asn
<220> FEATURE:
<221> NAME/KEY: MOD_RES
<222> LOCATION: (238)..(238)
<223> OTHER INFORMATION: Ala or Asn
<220> FEATURE:
<221> NAME/KEY: MOD_RES
<222> LOCATION: (247)..(247)
<223> OTHER INFORMATION: Gly or Asn

<400> SEQUENCE: 20

Thr Arg His Gln Asp Gly Arg Gln Asn Gln Ser Ser Leu Ser Pro Val
1               5                   10                  15

Leu Leu Pro Arg Asn Gln Xaa Glu Leu Pro Thr Gly Asn His Glu Glu
            20                  25                  30

Ala Glu Glu Lys Pro Asp Leu Phe Val Ala Val Pro His Leu Val Ala
        35                  40                  45

Thr Ser Pro Ala Gly Glu Gly Gln Arg Gln Arg Glu Lys Met Leu Ser
    50                  55                  60

Arg Phe Gly Arg Phe Trp Lys Lys Pro Glu Arg Glu Met His Pro Ser
65                  70                  75                  80

Arg Asp Ser Asp Ser Glu Pro Phe Pro Pro Gly Thr Gln Ser Leu Ile
```

```
                     85                  90                  95
Gln Pro Ile Asp Gly Met Lys Met Glu Lys Ser Pro Leu Arg Glu Glu
            100                 105                 110

Ala Lys Lys Phe Trp His His Phe Met Phe Xaa Lys Thr Pro Ala Ser
            115                 120                 125

Gln Gly Val Ile Leu Pro Ile Lys Ser His Glu Val His Trp Glu Thr
            130                 135                 140

Cys Arg Thr Val Pro Phe Ser Gln Thr Ile Thr His Glu Gly Cys Glu
145                 150                 155                 160

Lys Val Val Val Gln Asn Asn Leu Cys Phe Gly Lys Cys Gly Ser Val
                165                 170                 175

His Phe Pro Gly Ala Ala Gln His Ser His Thr Ser Cys Ser His Cys
            180                 185                 190

Leu Pro Ala Lys Phe Thr Thr Met His Leu Pro Leu Asn Cys Thr Glu
            195                 200                 205

Leu Ser Ser Val Ile Lys Val Val Met Leu Val Glu Glu Cys Gln Cys
            210                 215                 220

Lys Val Lys Thr Glu His Glu Asp Gly His Ile Leu His Xaa Gly Ser
225                 230                 235                 240

Gln Asp Ser Phe Ile Pro Xaa Val Ser Ala Thr Gly
            245                 250

<210> SEQ ID NO 21
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (55)..(55)
<223> OTHER INFORMATION: Arg or Asn
<220> FEATURE:
<221> NAME/KEY: MOD_RES
<222> LOCATION: (57)..(57)
<223> OTHER INFORMATION: Gln or Thr
<220> FEATURE:
<221> NAME/KEY: MOD_RES
<222> LOCATION: (131)..(131)
<223> OTHER INFORMATION: Arg or Asn
<220> FEATURE:
<221> NAME/KEY: MOD_RES
<222> LOCATION: (133)..(133)
<223> OTHER INFORMATION: Arg or Thr
<220> FEATURE:
<221> NAME/KEY: MOD_RES
<222> LOCATION: (150)..(150)
<223> OTHER INFORMATION: Arg or Asn
<220> FEATURE:
<221> NAME/KEY: MOD_RES
<222> LOCATION: (151)..(151)
<223> OTHER INFORMATION: Arg or Ala
<220> FEATURE:
<221> NAME/KEY: MOD_RES
<222> LOCATION: (152)..(152)
<223> OTHER INFORMATION: Val or Ser

<400> SEQUENCE: 21

Gly Arg Pro Glu Pro Gln Ser Pro Arg Pro Gln Ser Trp Ala Ala Ala
1               5                   10                  15

Asn Gln Thr Trp Ala Leu Gly Pro Gly Ala Leu Pro Leu Val Pro
            20                  25                  30

Ala Ser Ala Leu Gly Ser Trp Lys Ala Phe Leu Gly Leu Gln Lys Ala
            35                  40                  45
```

```
Arg Gln Leu Gly Met Gly Xaa Leu Xaa Arg Gly Gln Asp Glu Val Ala
         50                  55                  60
Ala Val Thr Leu Pro Leu Asn Pro Gln Glu Val Ile Gln Gly Met Cys
 65                  70                  75                  80
Lys Ala Val Pro Phe Val Gln Val Phe Ser Arg Pro Gly Cys Ser Ala
                 85                  90                  95
Ile Arg Leu Arg Asn His Leu Cys Phe Gly His Cys Ser Ser Leu Tyr
            100                 105                 110
Ile Pro Gly Ser Asp Pro Thr Pro Leu Val Leu Cys Asn Ser Cys Met
            115                 120                 125
Pro Ala Xaa Lys Xaa Trp Ala Pro Val Val Leu Trp Cys Leu Thr Gly
        130                 135                 140
Ser Ser Ala Ser Arg Xaa Xaa Xaa Lys Ile Ser Thr Met Leu Ile Glu
145                 150                 155                 160
Gly Cys His Cys Ser Pro Lys Ala
                165

<210> SEQ ID NO 22
<211> LENGTH: 7
<212> TYPE: PRT
<213> ORGANISM: Homo sapiens

<400> SEQUENCE: 22

Ser His Cys Leu Pro Ala Lys
1               5

<210> SEQ ID NO 23
<211> LENGTH: 6
<212> TYPE: PRT
<213> ORGANISM: Homo sapiens

<400> SEQUENCE: 23

Met Phe Arg Lys Thr Pro
1               5

<210> SEQ ID NO 24
<211> LENGTH: 6
<212> TYPE: PRT
<213> ORGANISM: Homo sapiens

<400> SEQUENCE: 24

Asn Gln Arg Glu Leu Pro
1               5

<210> SEQ ID NO 25
<211> LENGTH: 6
<212> TYPE: PRT
<213> ORGANISM: Homo sapiens

<400> SEQUENCE: 25

Pro Ala Arg Lys Arg Trp
1               5

<210> SEQ ID NO 26
<211> LENGTH: 6
<212> TYPE: PRT
<213> ORGANISM: Homo sapiens

<400> SEQUENCE: 26

Ser Arg Arg Arg Val Lys
1               5
```

```
<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Gly Gly Gly
1

<210> SEQ ID NO 28
<211> LENGTH: 6
<212> TYPE: PRT
<213> ORGANISM: Homo sapiens

<400> SEQUENCE: 28

Ser His Cys Leu Pro Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 29

Asn Gln Xaa Glu Leu Pro
1               5

<210> SEQ ID NO 30
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
agccagacaa gccagacaag ccagacaagc cagacaagcc agacaagcca gacaagccag      60
acaagccaga caagccagac aagccagaca agccagacaa gccagaca                  108
```